United States Patent [19]

Suzuki

[11] Patent Number: 5,576,090
[45] Date of Patent: Nov. 19, 1996

[54] SHEET ELASTIC COMPLEX USED IN SANITARY PRODUCTS ITS MANUFACTURING PROCESS, AND ITS USAGES

[76] Inventor: Migaku Suzuki, 4-301 Arusu Kamakura, 19-2 Ueki, Kamakura Kanagawa, Japan

[21] Appl. No.: 17,505

[22] Filed: Feb. 12, 1993

[30] Foreign Application Priority Data

| Feb. 13, 1992 | [JP] | Japan | 4-026818 |
| Feb. 24, 1992 | [JP] | Japan | 4-035467 |
| Aug. 18, 1992 | [JP] | Japan | 4-219127 |

[51] Int. Cl.$^6$ .............. A61F 13/15; B32B 3/28; B32B 31/08; B32B 31/20
[52] U.S. Cl. .................. 428/152; 2/76; 2/78.3; 2/221; 2/237; 2/401; 156/73.1; 156/73.5; 156/85; 156/164; 156/199; 156/229; 156/290; 428/163; 428/166; 428/192; 428/200; 428/201; 428/286; 428/332; 604/378; 604/380; 604/385.2
[58] Field of Search .................. 156/73.1, 73.5, 156/85, 164, 199, 229, 290; 604/378, 380, 385.7

[56] References Cited

U.S. PATENT DOCUMENTS 4,525,407  1/1985  Ness ........................ 428/138
4,781,966  11/1988  Taylor.
4,883,549  11/1989  Frost.
4,891,285  1/1990  Fahrenkrug.
4,908,247  3/1990  Baird et al..

FOREIGN PATENT DOCUMENTS

91/15355  10/1991  WIPO.

*Primary Examiner*—James C. Cannon
*Attorney, Agent, or Firm*—Dressler, Goldsmith, Milnamow & Katz, Ltd.

[57] ABSTRACT

This invention provides an exceptionally expandable sheet elastic complex which consists of an elastic body sheet and a sheet backing material which is mounted on either one or both sides of it, these two members being bonded together along multiple, oblong, mutually parallel bonding sections, and in which multiple, mutually parallel channels are formed between the two members because the width of the sheet backing material between mutually adjacent bonding sections is greater than that of the elastic body sheet. The sheet backing material does not accept more than the minimum constraint of the elastic body sheet, and its waveform surface has excellent properties as a material for use in sanitary products. The invention also provides a process for manufacturing this sheet elastic complex.

52 Claims, 14 Drawing Sheets

MACHINE DIRECTION

MACHINE DIRECTION

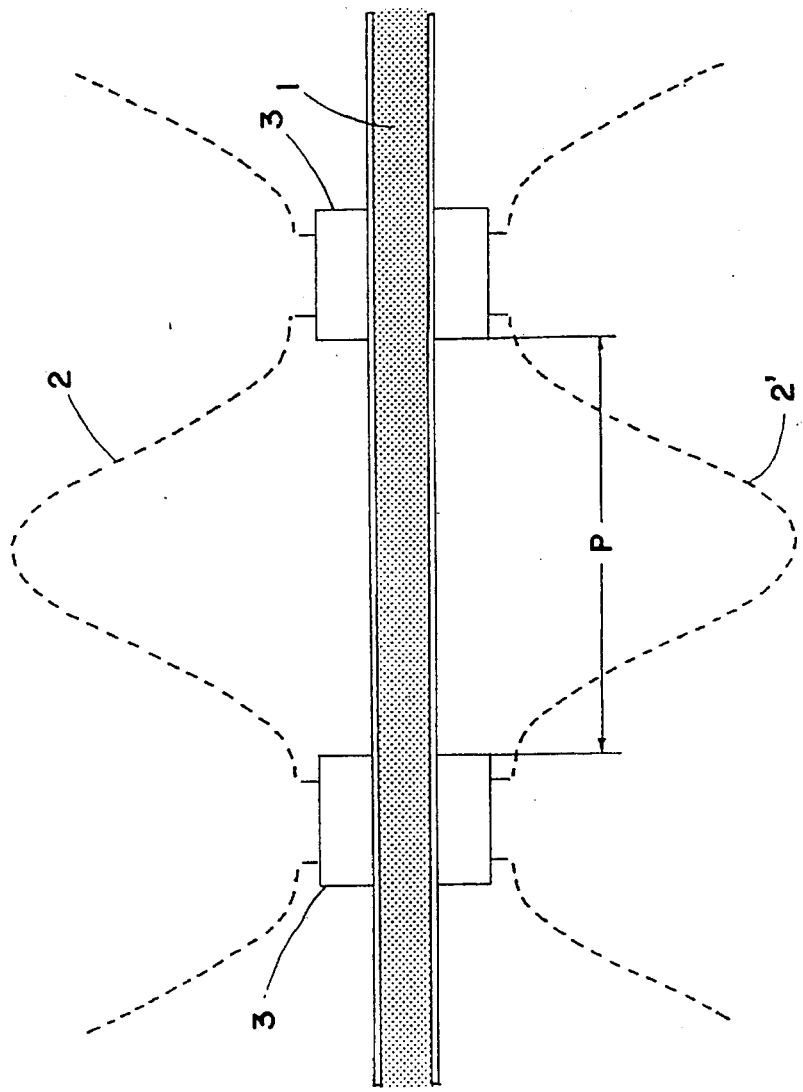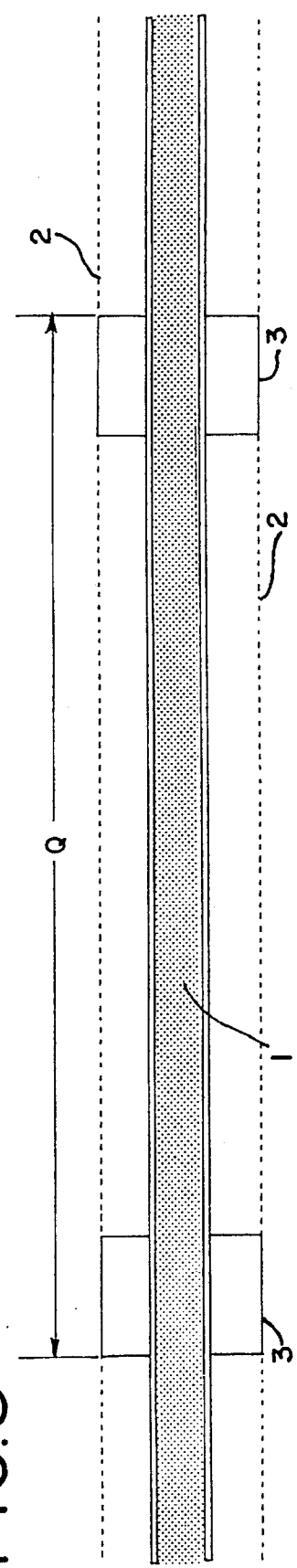
FIG.7
FIG.8

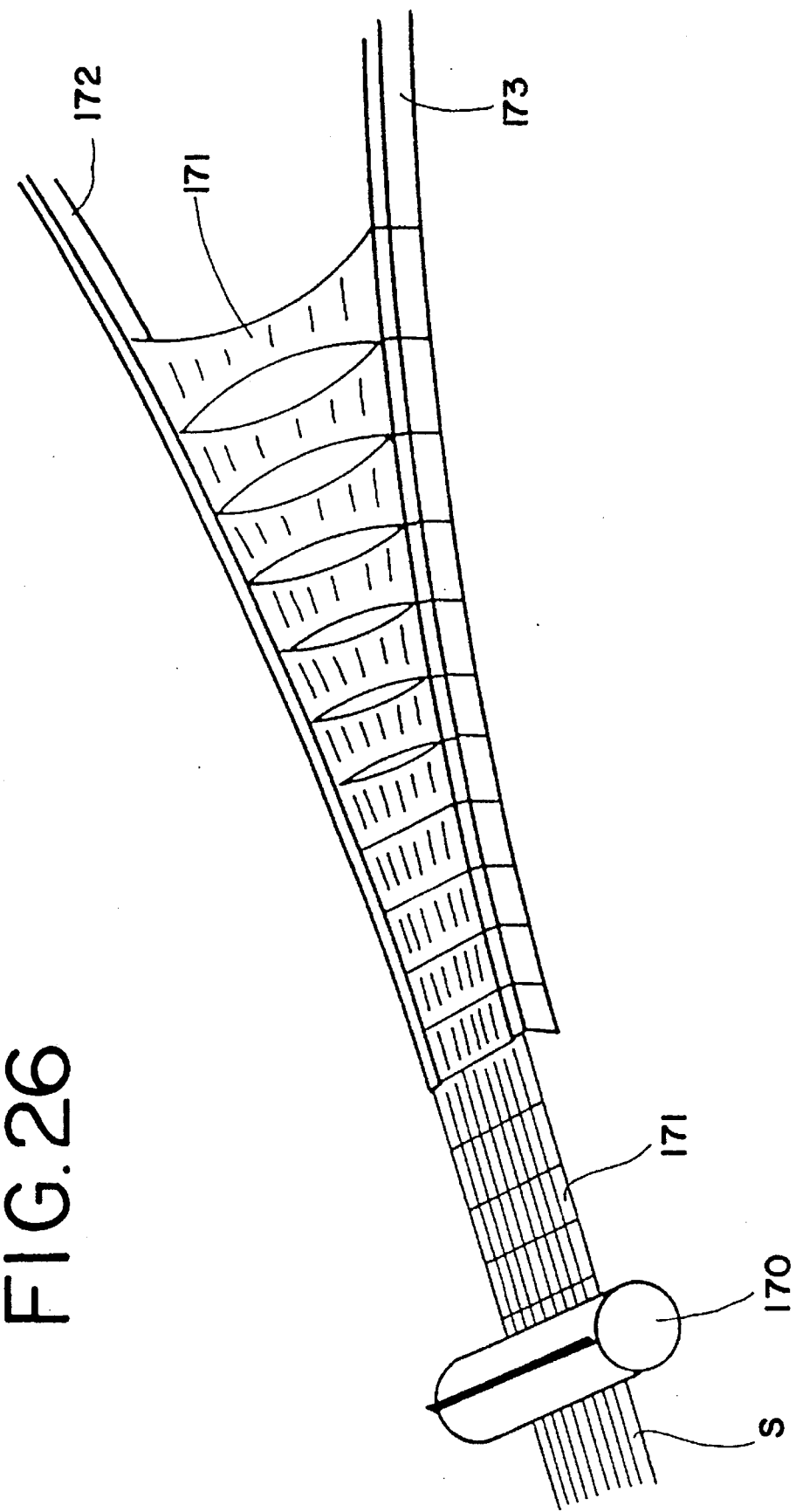

SHEET ELASTIC COMPLEX USED IN SANITARY PRODUCTS ITS MANUFACTURING PROCESS, AND ITS USAGES

TECHNICAL FIELD

This invention concerns a sheet elastic complex compounded from an elastic sheet and a sheet backing forming channels. More specifically, this sheet elastic complex is soft, comfortable, and highly waterproof, being used next to the skin as a liquid-impermeable material. The invention also concerns the process for manufacturing this sheet elastic complex, and furthermore concerns any form of sanitary articles, in particular diapers and sanitary napkins, which are made from this type of product.

BACKGROUND OF THE INVENTION

Many types of elastic materials are used in daily necessities such as underwear and socks, in the waist and crotch of disposable diapers, in elastic bandages, and in the sleeve cuffs of surgical gowns. They are used to strengthen and improve the adhesion of these products to the human body. Materials commonly used in these capacities are elastic bodies such as natural, synthetic, or polyurethane rubber, in the form of filaments, foam, film, or netting, and covered in cloth, non-woven fabric, or a filamentous covering to prevent the elastic body from coming in direct contact with the skin.

The best known expandable material is a pleated elastic complex formed by elongating the elastic body, keeping it elongated while bonding the covering material to it through heat, ultrasound waves, or an adhesive agent, then releasing the tension in the bonded body. The elastic body used in the waist and crotch of disposable diapers currently on the market is this type of material.

Another common expandable material is an elastic complex. This is formed by using ultrasound waves or an adhesive agent to bond a potential elastic body having characteristics of heat contractibility with an unelongatable material. The bonded body is then processed in its tension-free state within a hot ambient atmosphere and the potential elastic body contracted.

Additionally, JPA Sho 59-5990 disclosed another technique for obtaining an elastic complex. The technique involves partially, or discontinuously, bonding a net-form elastic body in a relaxed state with an unelongatable backing material having an elongatability relatively lower than film containing PE and EVA. The partially bonded body is elongated to the necessary extent under high tension, within the allowable elongation range of the backing material. Next, a larger permanent distortion is made in the non-bonded portion of the backing than is made in the bonded portion. The tension is then released from this elongated bonded body to return the elastic body to a relaxed state. In this manner, the elastic complex possesses expandability. It has been noted that elastic complexes made through the three conventional techniques described above all have the disadvantage of insufficient suppleness and comfort against the skin. These complexes are thus unsatisfactory materials for products such as diapers and sanitary napkins which stay in contact with the skin for long periods of time.

In general, liquid impermeability and gas permeability, or breathability, are opposing conditions. Enhancing the one results in diminishing the other. Conventional techniques have not created a material which can satisfy both of these conditions simultaneously. Existing products are also unsatisfactory from the viewpoint of industrial manufacturing, in which the ease and low cost of manufacturing are important elements.

Ideally, to solve these problems without causing a deterioration in absorption or other types of performance and without causing a price increase, the backing at the edges of the waist and the elastic body should not be in direct contact, allowing full use of the elastic body's expansion strength. One method of achieving this is to use a floating structure, suspending the elastic body from the edge backing in a floating fashion. In forming the floating structure, there should be as few as possible points of bonding between the backing material and the elastic body, but a certain number will be required to give the structure an even distribution of elasticity.

The purpose of this invention is to provide a sheet elastic complex which has sufficient elasticity for sanitary products such as diapers and which does not allow for any essential diminishment in liquid absorption performance, as the elastic body is attached in such a way as to hold a floating structure.

SUMMARY OF THE INVENTION

This invention provides a sheet elastic complex which contains an elastic body sheet which is equipped with a sheet backing mounted on at least one side of the above-mentioned elastic sheet, in which the above-mentioned elastic body sheet and sheet backing are bonded together along multiple, oblong, and mutually parallel bonding sections, and in which the width of the above-mentioned sheet backing material between the above-mentioned mutually adjacent bonding sections is greater than that of the above-mentioned elastic body sheet, thus forming multiple, mutually parallel channels between the two members.

Furthermore, this invention provides a diaper in which the above-mentioned sheet elastic complex is affixed to sections such as the waist and crotch where expandability is desired.

This invention also provides underpants-shaped sanitary products in which essentially all parts are composed of a sheet elastic complex.

The sheet elastic complex in this invention can maintain the correct floating structure so as to offer full elastic performance while exhibiting no diminishment in liquid absorption performance.

Furthermore, this invention provides a process for manufacturing a sheet elastic complex which includes a process for mounting sheet backing material on at least one side of an elastic body sheet; a process for bonding the above-mentioned sheet backing material and elastic body sheet at multiple, oblong, and mutually parallel bonding sections; and a process for forming multiple, mutually parallel channels between the above-mentioned sheet backing material and each of the above-mentioned elastic body sheets in the bonded body obtained in the above process, the channels being formed through stretching the above-mentioned sheet backing material past its extension limit in a direction orthogonal to the lengthwise direction of the above-mentioned bonding sections, thus ensuring that the width of the above-mentioned backing material between the mutually adjacent above-mentioned bonding sections is greater than that of the above-mentioned elastic body sheet.

BRIEF DESCRIPTION OF THE DIAGRAMS

Figure 3:
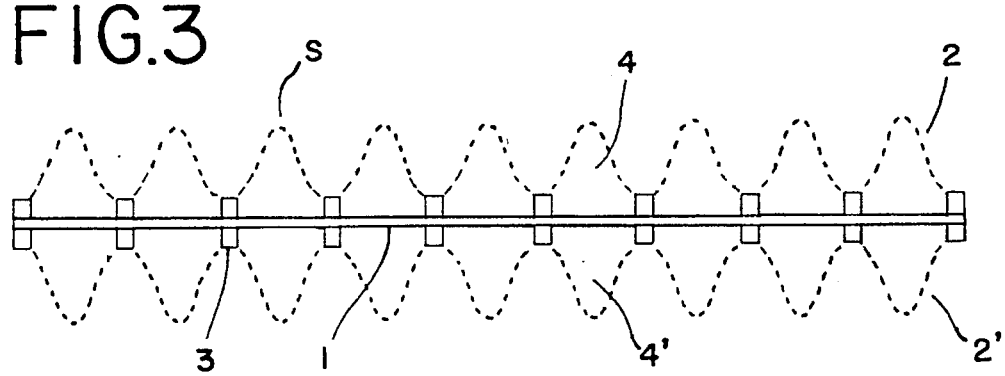
Figure 4:
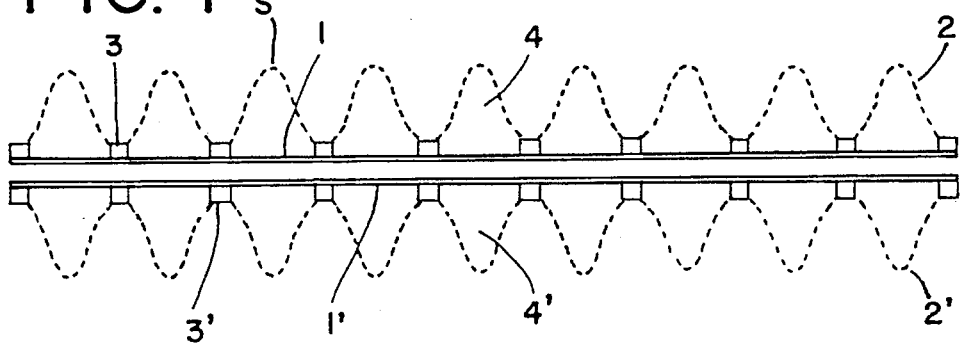

FIGS. 3 and 4 each show one of the other sheet elastic complex examples in this invention.

Figure 5A:
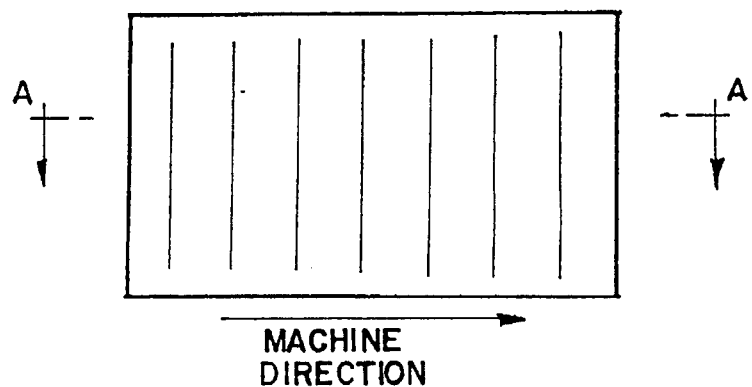
Figure 5B:
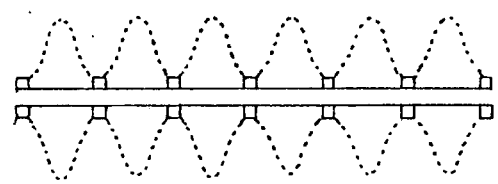

FIG. 5 shows a diaper in which the complex in this invention is applied.

Figure 6A:
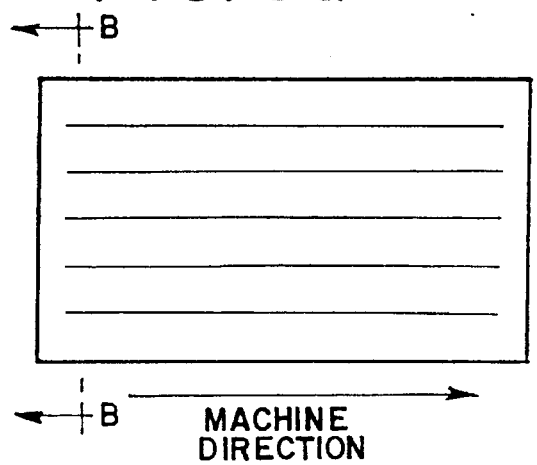
Figure 6B:
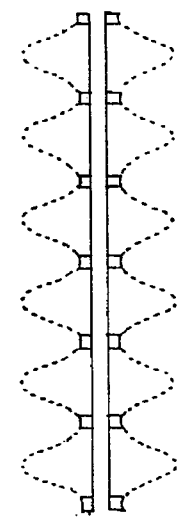
Figure 9A:
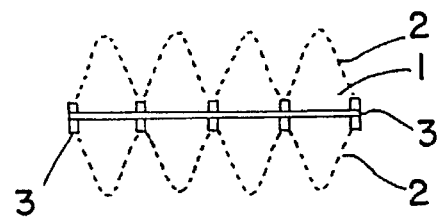
Figure 9B:
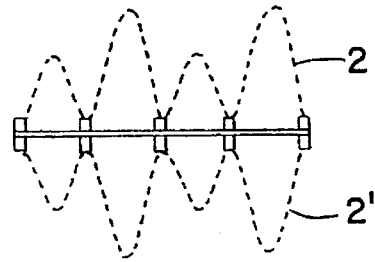
Figure 9C:
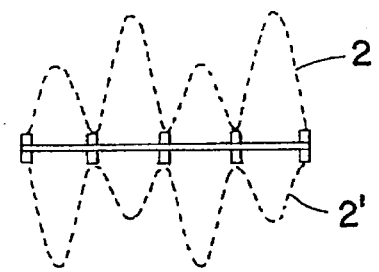
Figure 9D:
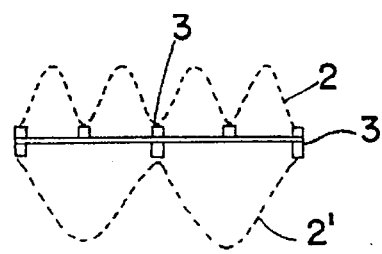
Figure 9E:
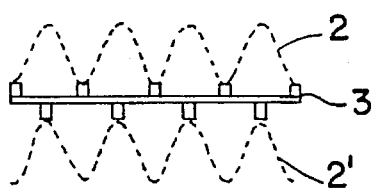
Figures 9F, 9G:
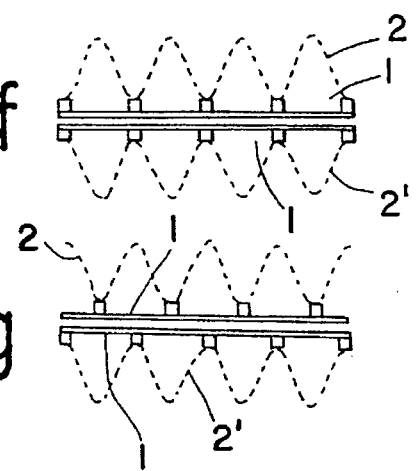

FIGS. 6 to 8 show other sheet elastic complexes.

FIG. 9 is a diagram explaining the elongation limit of the invention's elastic complex.

Figure 10A:
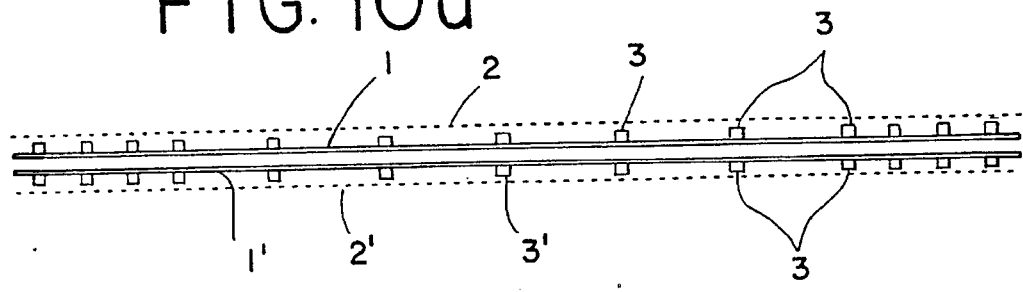
Figure 10B:
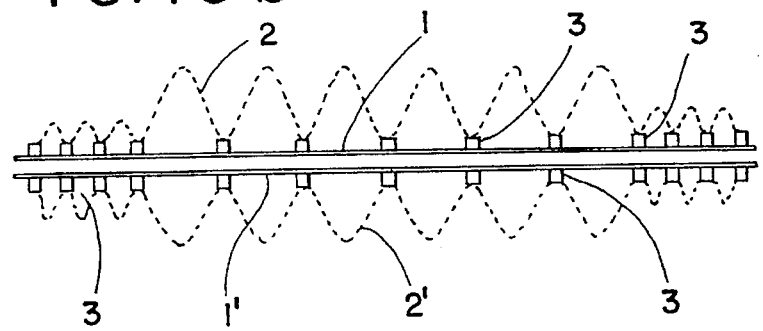

FIG. 10 shows examples of sheet elastic complexes having locally differing elongatability.

Figure 11A:
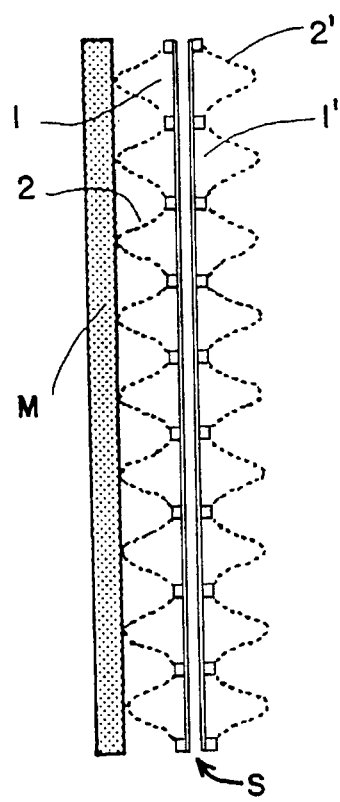
Figure 11B:
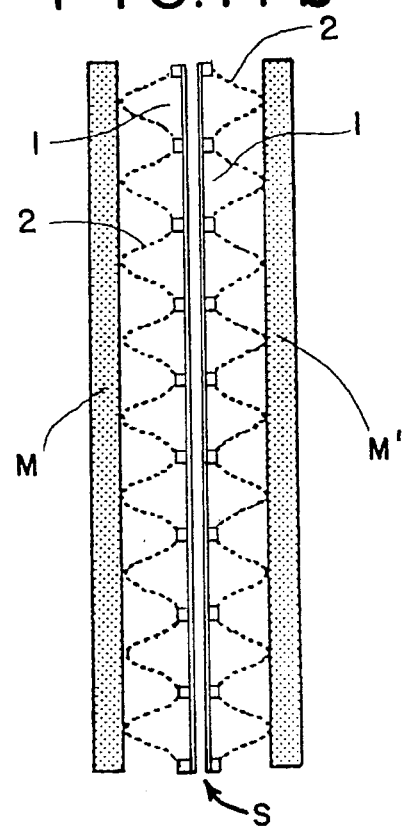

FIG. 11 shows more examples of sheet elastic complexes.

Figure 13:
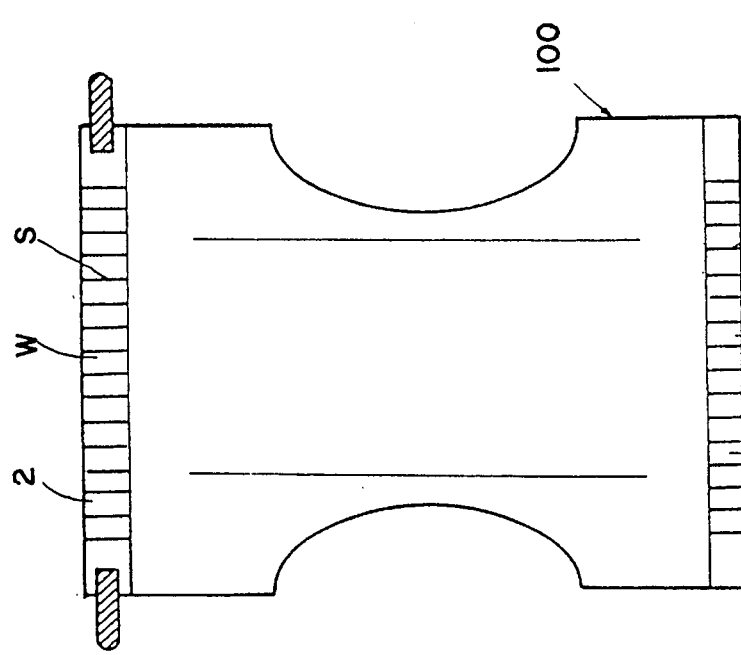
Figure 12A:
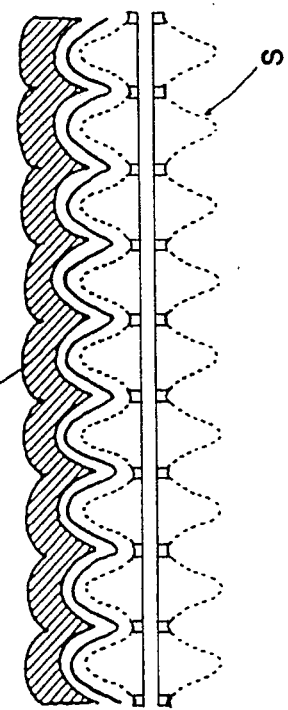
Figure 12B:
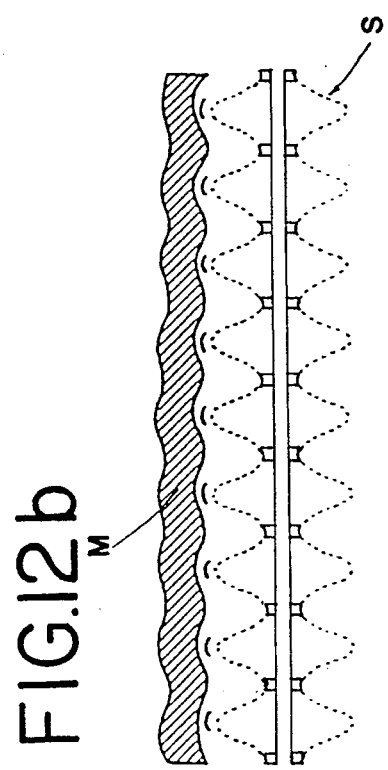

FIGS. 12 and 13 show a sheet material reflecting the waveform pattern of a sheet elastic complex.

Figure 14:
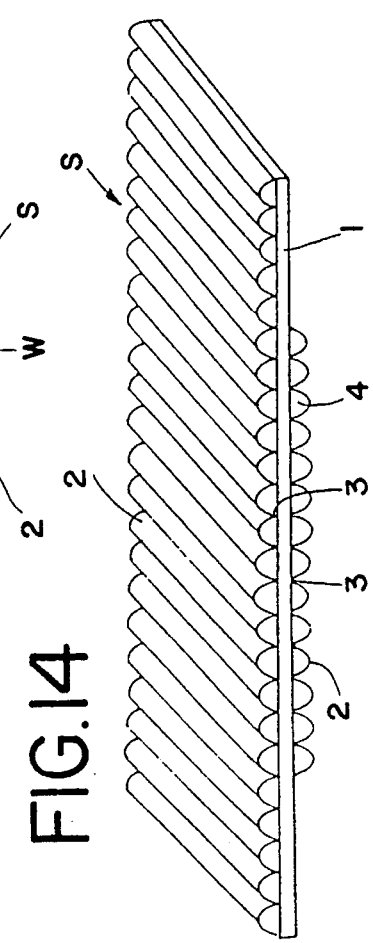

FIG. 14 shows a type of elongation test material.

Figure 15:
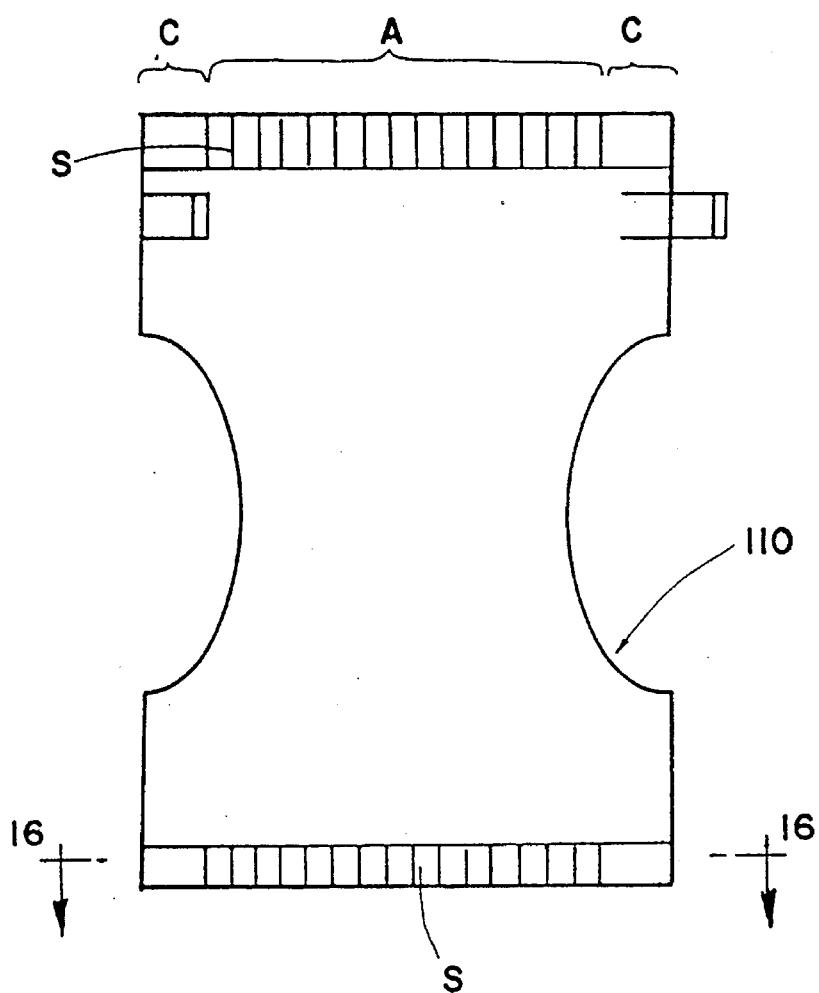
Figure 16:
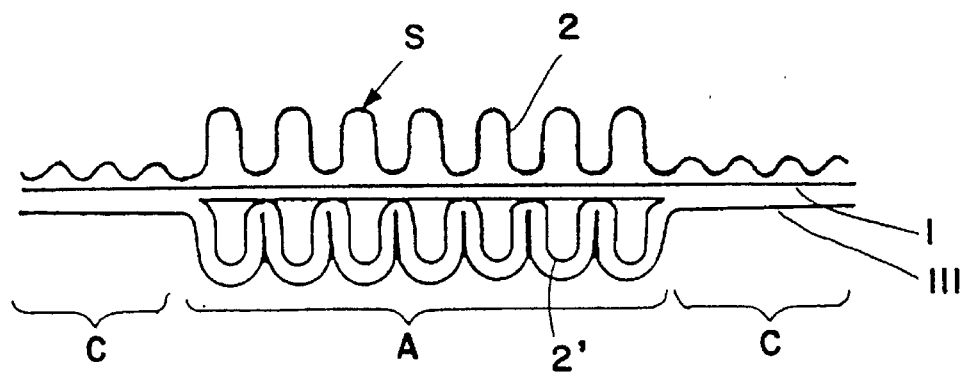

FIGS. 15 and 16 show a diaper in which the sheet elastic complex shown in FIG. 14 is applied.

Figure 17:
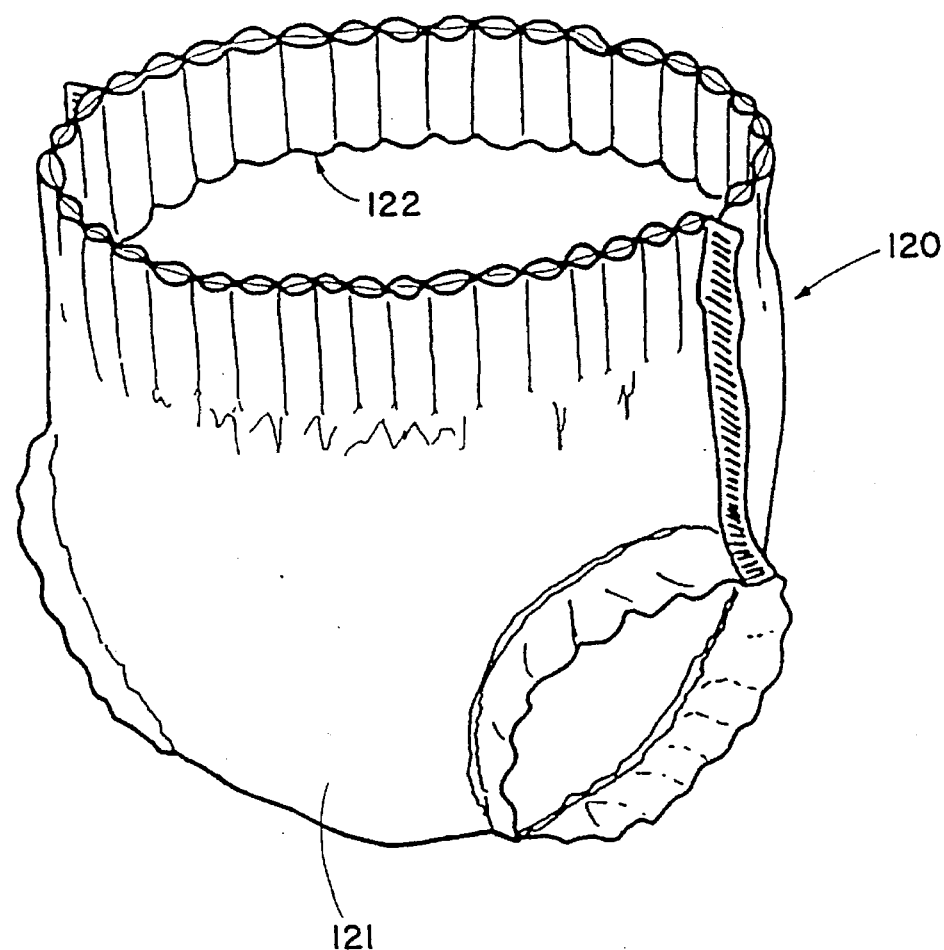

FIG. 17 is an oblique diagram showing an underpants-type sanitary product constructed from the sheet elastic complex of this invention.

Figure 18:
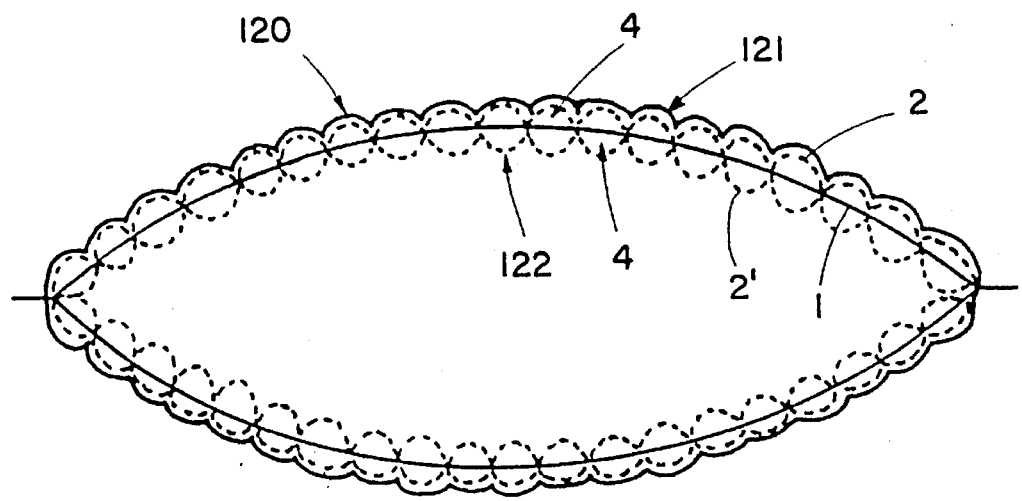

FIG. 18 is a cross-sectional diagram along the A—A line of FIG. 17.

Figure 19:
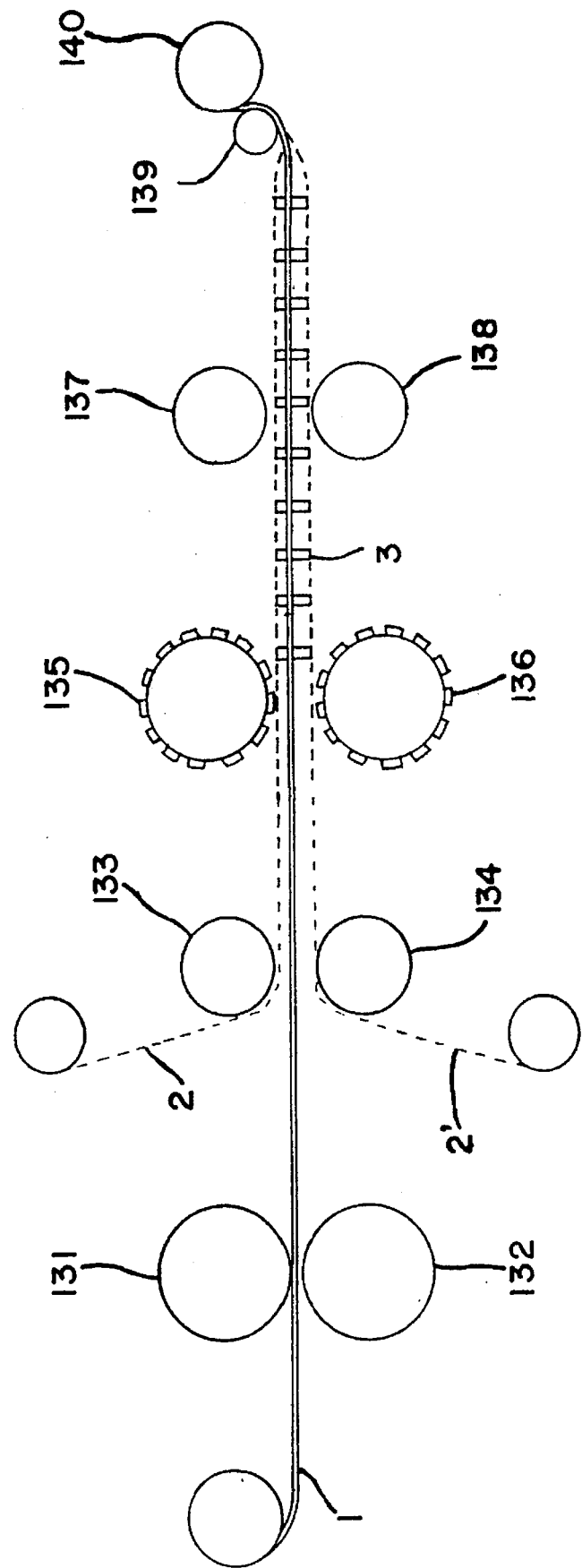

FIG. 19 shows the process for manufacturing the sheet elastic complex of this invention.

Figure 20:
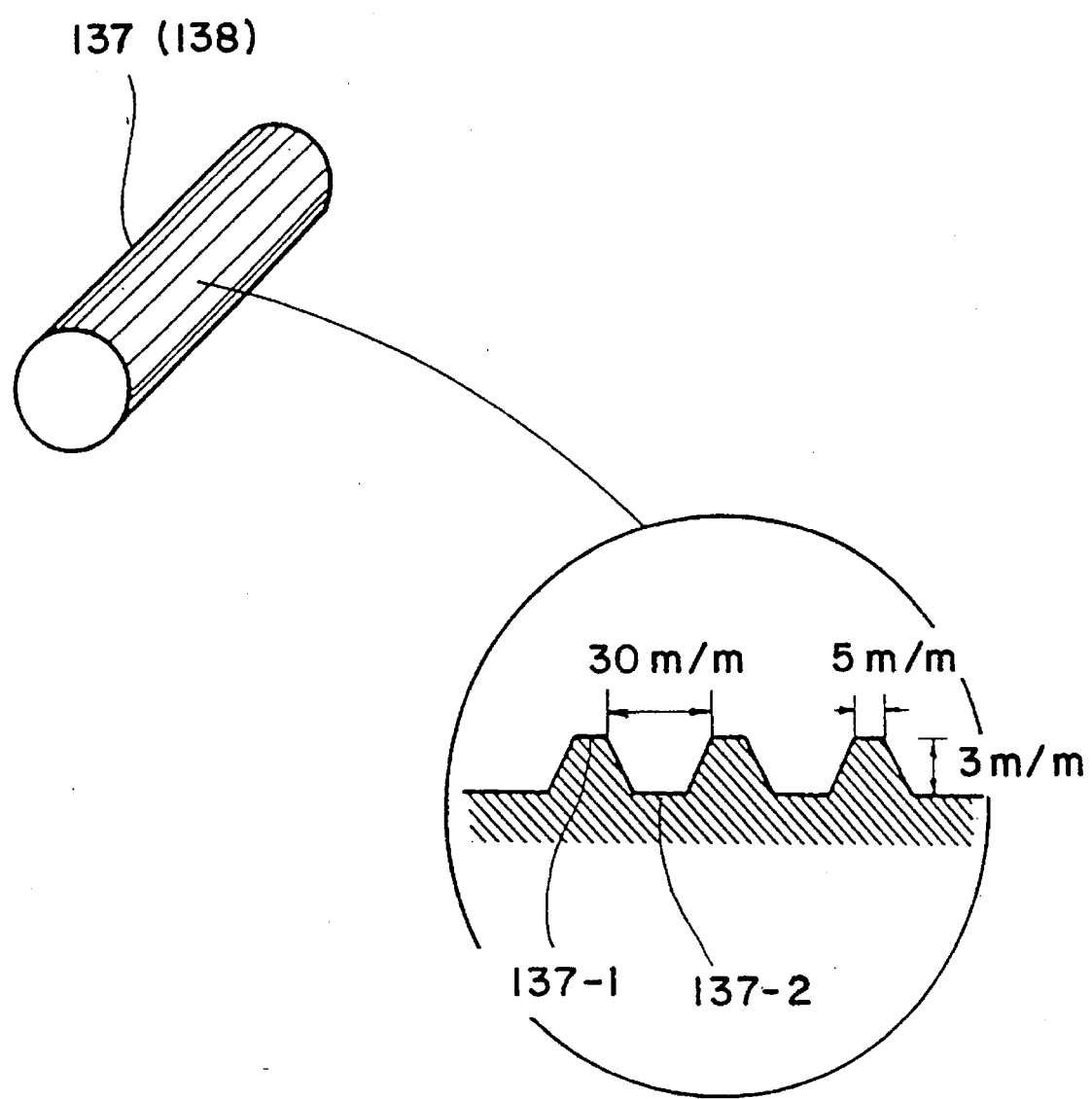

FIG. 20 shows the heated grid roll used in the process shown in FIG. 19.

Figure 21:
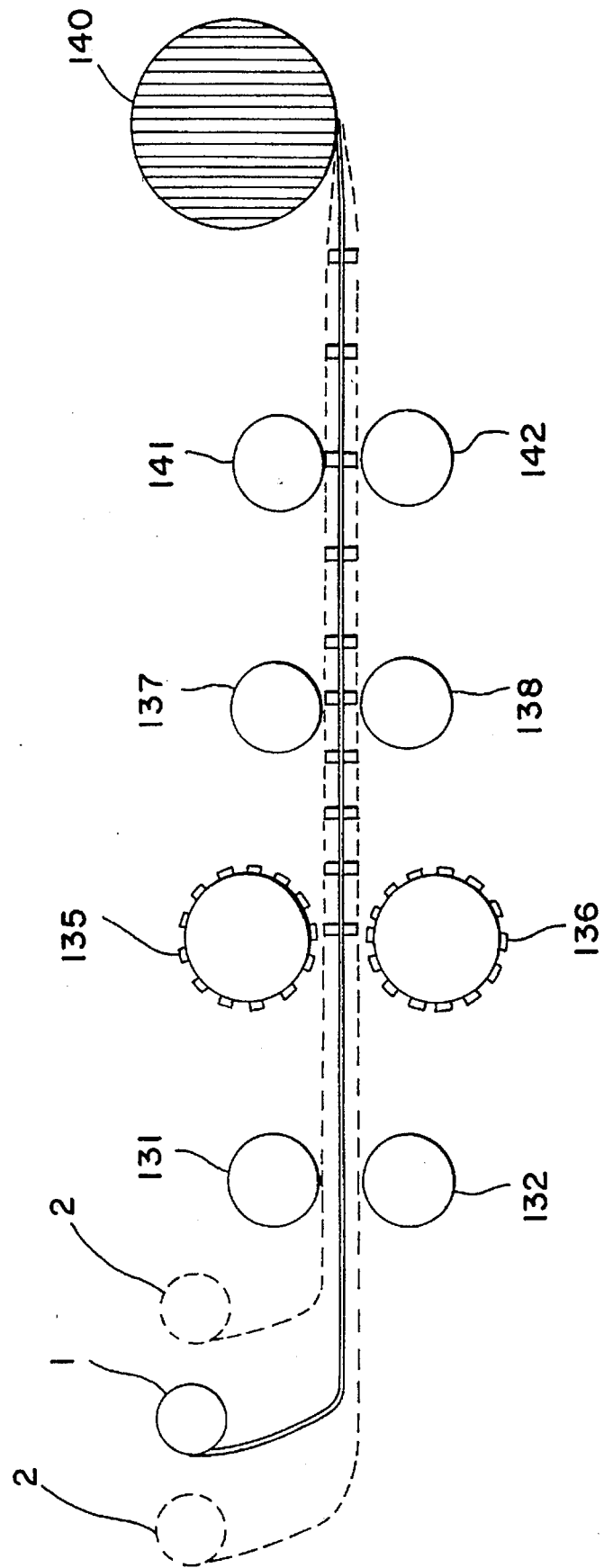

FIG. 21 is a process drawing of another method for manufacturing the sheet elastic complex for this invention.

Figure 22:
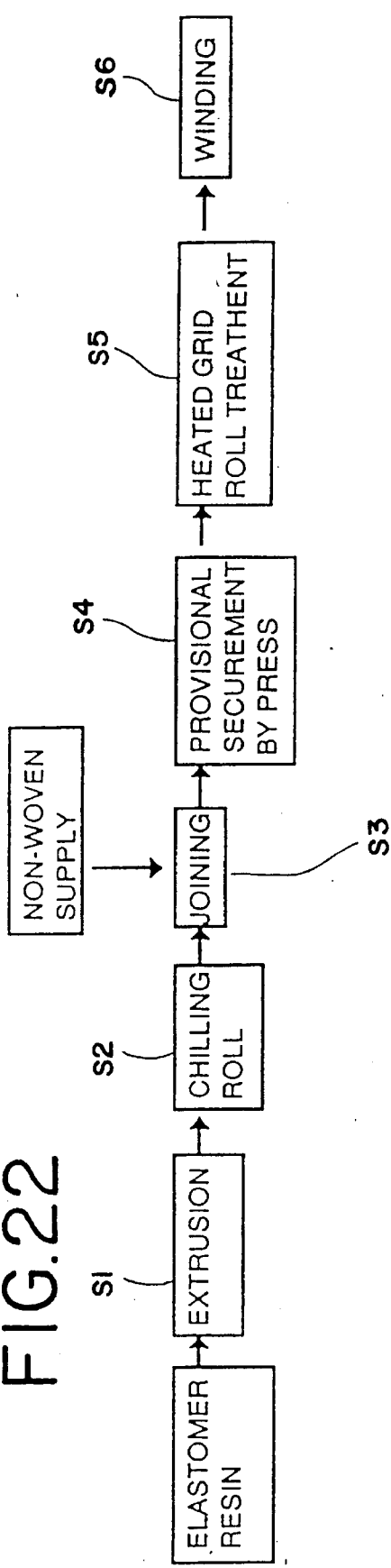

FIG. 22 is a process drawing for another method for this invention.

Figure 23:
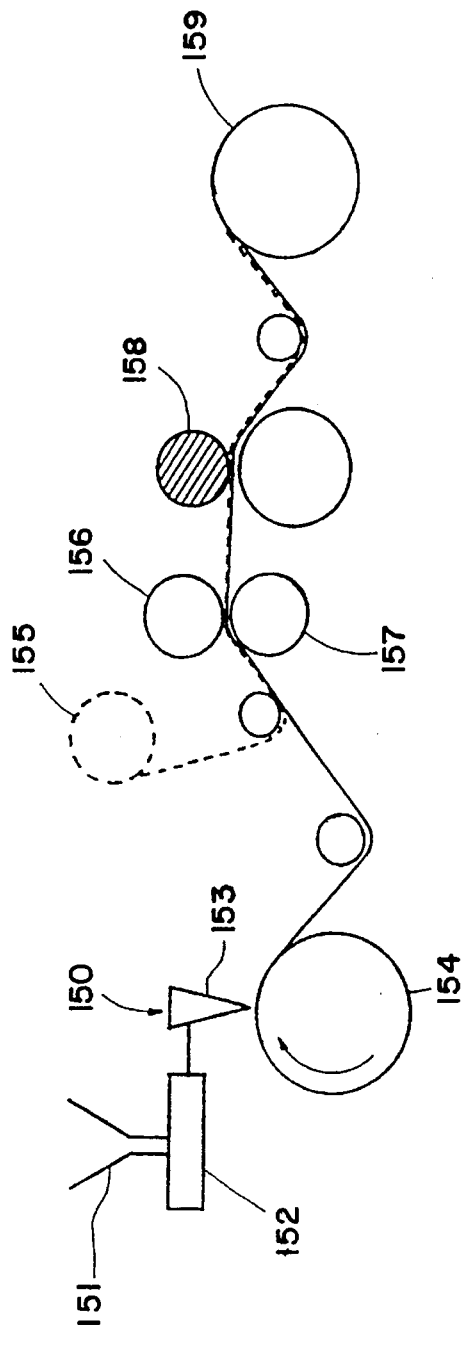

FIG. 23 schematically illustrates the equipment used to implement the process shown in FIG. 22.

Figure 24:
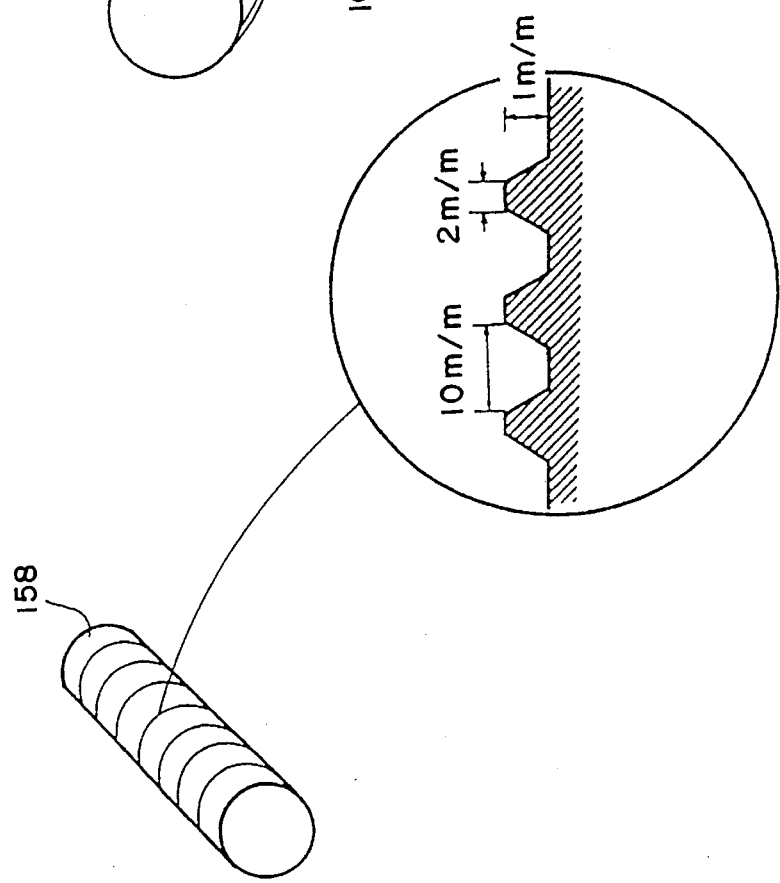

FIG. 24 shows the heated grid roll used in the process shown in FIG. 22.

Figure 25:
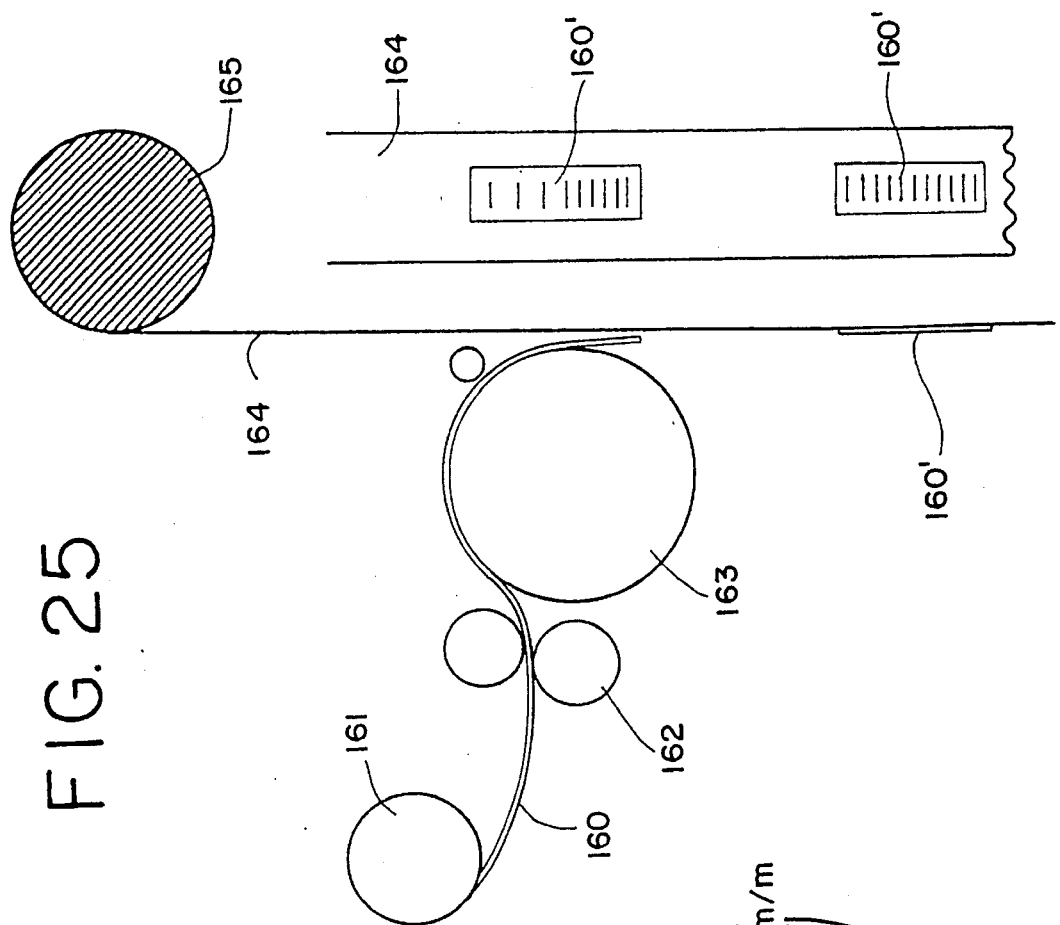

FIG. 25 is a process diagram showing one example of the process of applying the elastic complex which becomes this invention and has expandability in the machine direction.

FIG. 26 shows the sheet elastic complex which becomes this invention and has expandability in the cross direction.

DETAILED DESCRIPTION OF THE INVENTION

In the sheet elastic complex of the invention described above, the sheet backing material is longer than the elastic body sheet between the mutually adjacent bonding sections. Thus when the sheet elastic complex is stretched in the widthwise direction of the channels, the elastic body sheet alone stretches until the sheet backing is elongated. Therefore, even if the sheet backing material used possesses virtually no expandability at all, the complex will have an extremely large range of expandability in the widthwise direction of the channels.

The most suitable process for forming the above-mentioned channels is to superpose the sheet backing material and the elastic body sheet, then to bond them together at the bonding sections, using, for instance, a heated roll set to specified intervals.

Sheet materials are generally divided into two major categories. Those of the first type, particularly materials having extensibility, have almost the same properties in the machine direction, or the direction in which the machine discharges the material during production, and in the cross direction, or that direction orthogonal to the machine direction. Those of the second type have a markedly greater extensibility in the cross direction than in the machine direction. This latter type of sheet material is used advantageously as the sheet backing material for the sheet elastic complex of this invention. This sheet backing material should be bonded to the elastic body sheet with the machine direction of the material aligned with the channel direction.

A complex with such a structure has a great extensibility in the cross direction, so that after the elastic body sheet and the sheet backing are superposed in a flat state and affixed along the desired lines of bonding, channels will form when the entire piece is elongated in the direction orthogonal to the lengthwise direction of the lines of bonding, then released. Elongation at a moderate rate, that is at a rate greater than the elongation recovery limit and less than the elongation limit in this direction of the sheet backing material used, will cause permanent distortion in the form of greater length in the sheet backing in the areas between the lines of bonding. This is where the channels form.

The first function of the channels formed between the elastic body sheet and the sheet backing of the sheet elastic complex of this invention is to provide the sheet backing with a structural suppleness. This makes it extremely useful as a material for products such as diapers and sanitary napkins which stay in contact with the skin for long periods of time.

Second, the channels extend continuously between the elastic body sheet and the sheet backing, ensuring high breathability through the channels. This eliminates the stuffiness and other discomforts peculiar to impermeable sheets, making this material the most suitable for all types of products worn next to the skin.

Third, the channels provide widely differing resistance in their lengthwise and widthwise directions to fluid flowing on the outer surface of the sheet backing. In other words, fluid flowing lengthwise along the channels meets very little resistance, while that flowing widthwise faces a remarkably great resistance. This resistance-related anisotropy results in a superior horizontal leakage prevention effect when the sheet elastic complex is used in, for instance, the horizontal leakage prevention side barriers of sanitary napkins.

And fourth, the air existing within the channels enhances the adiabatic properties both inside and outside the sheet elastic complex.

The sheet backing may be affixed to both sides of one elastic body sheet, or the complex may be constructed by affixing sheet backing, forming channels, to one side each of two elastic body sheets, then superposing these two sheets together so that the sheet backing faces outward.

When sheet backing is affixed to the two sides of one elastic body sheet, the points of affixation of the elastic body sheet and the sheet backing should be in approximately the same position on both sides. Also, the height of the channels can be lower at the two ends than in the center region. And when sheet backing is affixed to both sides of an elastic body sheet, one side of the sheet backing can be set partially against the elongation direction of the elastic body sheet.

Many types of non-woven fabric are suitable for this sheet backing. Sometimes liquid-impermeable materials are used. If non-woven fabric is appropriate for the particular application of the sheet elastic complex, then any type of non-woven fabric will suffice. However, two particularly appropriate types of non-woven fabrics are those obtained by bonding parallel card weave in a high-pressure water jet, and those obtained by separately weaving filaments or tows. The fibers in these non-woven fabrics are oriented relatively more in the machine direction, giving the fabrics a markedly greater extensibility in the cross direction than in the machine direction. One non-woven fabric belonging to this group and suitable for use in this invention is that obtained through the water-jet process. This fiber is quite ductile, yet is still very strong and tough. The raw fibers used in the non-woven fiber should be a 1.5 d to 3 d synthetic fiber staple made of hydrophobic fibers such as PE, PP, and PET, which have low water leakage and do not irritate the skin, yet which are highly safe.

Rayon, cotton, or other hydrophilic fibers may, in certain cases, be added to aid in the absorption of perspiration. However, the blend should contain no more than fifty percent of such fibers to maintain good heated adhesiveness with the elastic film. For the rayon, cotton or other hydrophilic fibers, a fiber with particularly strong antibacterial properties might be used, for instance brand names such as "Kitoseru" or "Kitobori" (rayon and polynosic fibers made by Fuji Spinning Co., Ltd.). Another possibility would be fibers that both have water absorption properties and are effective in preventing rashes.

Preferable materials for a liquid-impermeable backing include nylon, polyester, or polyolefine films such as polyethylene, polypropylene, or vinyl acetate copolymer. Of these, the polyolefine materials are best for considerations such as cost.

Backing made from these materials would exhibit superior waterproofing properties if applied to any of the products in the invention.

Possible materials for the elastic body sheet in this invention include thin-layer sheets such as natural and synthetic rubber, or elastic body sheets such as polyurethane film, polyurethane melt-blown nonwoven fabric, styrene-butadiene block polymer film, and polyolefine elastomer film. However, considering properties such as adhesiveness to a low-cost backing, the best choice would be one or a synthetic rubber blend of polyolefine elastomers such as EVA, ultra-low density LLDPE, ethylene propylene elastomers, ethylene methyl acrylate elastomers, or a styrene-ethylene-butadiene-styrene block polymer (SEBS) blend, or a jointly extruded film of polyurethane elastomers and polyolefine elastomers. Polyolefine elastomers can be manufactured at a very low industrial cost, being characterized by an inexpensive resin and ease of molten extrusion molding. Furthermore, as described below, they can bonded to non-woven fabrics much more easily than through methods such as thermocompression bonding or ultrasonic bonding. The elastic body used in this invention does not require elasticity in the machine direction, in which the molecules are easily oriented. It need only have elasticity in the cross direction. The advantages to production in this sense are increasingly important.

Figure 1:
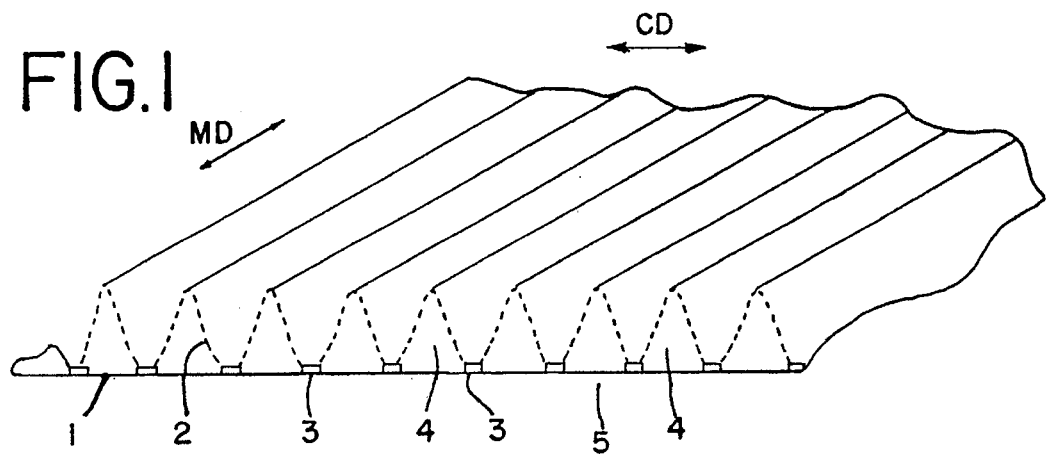
FIG. 1 is a partial, oblique diagram showing one example of the sheet elastic complex in this invention.
Figure 2:
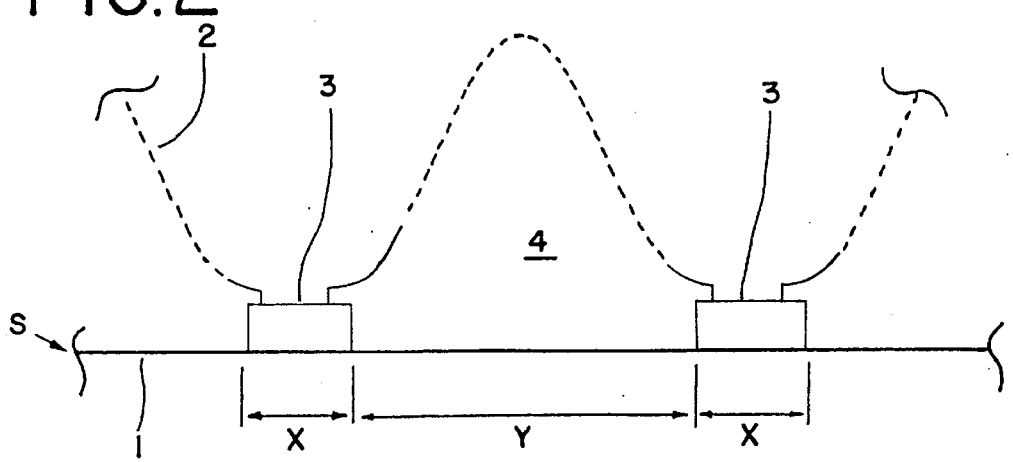
FIG. 2 is an enlarged, cross-sectional diagram of one part of the edge of the sheet elastic complex shown in figure one.

FIG. 1 is a partial, oblique diagram showing one example of the sheet elastic complex in this invention, and FIG. 2 is an enlarged, cross-sectional diagram of one part of that. In these two diagrams, the invention's sheet elastic complex 5 contains elastic body sheet 1 and a sheet backing, or non-woven fabric 2. These two components are affixed together along bonding lines 3, continuously in the first direction, or machine direction (MD) of non-woven fabric 2, and discontinuously in the approximately orthogonal second direction, or cross direction (CD).

The width of non-woven fabric 2 between the two adjacent bonding lines 3 and 3 is greater than that of elastic body sheet 1 between the same points. As a result, multiple channels 4 extending in the machine direction are formed between elastic body sheet 1 and non-woven fabric 2.

A comparison of width X of bonding sections 3 and width Y of non-bonding sections, as shown in FIG. 2, shows that as width X of the bonding sections increases, the strength of the complex increases, but, contrarily, the expansion elasticity decreases. It is important to select the appropriate ratio of bonding section width X to non-bonding section width Y, or $X/(X+Y)\times 100\%$. The value for width X should generally be greater than 0.5 mm. It should be between 1 mm and 10 mm, or even better, between 2 mm and 5 mm. Less than 0.5 mm tends to break or separate. Additionally, the ratio expressed as $$X/(X+Y)\times 100\%$$

should be less than 50%. If the ratio exceeds 50%, the expandability decreases, rendering the product unsuitable for practical use.

As for the process of bonding elastic body sheet 1 and non-woven fabric 2, the two may be bonded in lines or in bands using a pressure sensitive adhesive or an adhesive which has excellent bonding properties. However, from the standpoints of price and production process, it is better to use ultrasonic fusion or thermocompression bonding. The best method is to superpose the non-woven fiber on the elastic body sheet and bond the two together during the manufacturing process of the elastic body sheet, while it is still sticky.

There are no particular restrictions for devising a way to bond elastic body sheet 1 and non-woven fabric 2 so that they form channels 4. However, as already stated, it is possible to use a method of forming the channels which takes advantage of the difference in elongatability of the non-woven fabric in the machine direction and in the cross direction. In other words, it is possible to form the channels by first superposing non-woven fabric 2 on at least one side of elastic body sheet 1, bonding the two at bonding sections 3, continuously in the machine direction and discontinuously in the cross direction, stretching complex sheet 1 past the elastic limit of the non-woven fabric, then releasing the tension, thus causing a permanent extension of the non-woven fabric and making the width of the non-woven fabric between the bonding sections greater than that of the elastic body sheet.

The sheet elastic complex of this invention may be constructed not only as in FIGS. 1 and 2, in which the sheet backing is attached to only one side of the elastic body sheet. The invention also encompasses the sheet elastic complex 5 shown in FIG. 3, which is provided with sheet backing 2 and 2' attached to the two sides of elastic body sheet 1 and bonded to elastic body sheet 1 at the common bonding sections 3.

Or, the sheet elastic complex of this invention might also employ the structure shown in FIG. 4, in which the first member is composed of sheet backing 2 bonded to one side of elastic body sheet 1 at bonding sections 3, and the second member is composed of sheet backing 2' bonded to one side of elastic body sheet 1' at bonding sections 3', and in which elastic body sheets 1 and 1' are superposed so that they face each other.

The sheet elastic complexes shown in FIGS. 3 and 4 have the advantage of giving both sides the soft feel of a non-woven fabric-type sheet backing. However, if a greater degree of liquid-impermeability is desired, one side of the sheet backing may be replaced by a sheet made of liquid-impermeable material.

The elastic complex of the invention can be expandable in either the machine or the cross direction, depending on its purpose or the position in which it is used. The sheet elastic complex shown in (a) and (b) of FIG. 5 is expandable in the machine direction and is suitable for use in, for example, the crotch gathers of a diaper. On the other hand, the sheet elastic complex shown in (a) and (b) of FIG. 6 is expandable in the cross direction and is suitable for use in, for example, in the waist gathers of a diaper.

The extent of elongatability of the elastic body sheet and the sheet backing determine the expansion performance of the invention's sheet elastic complex. Here we define the elongation limit as the elongation immediately prior to the elongation breaking point. If the elongation limit of the elastic body sheet is 200%, and the elongation limit of the non-woven fabric is 100%, then the resulting elastic complex will have an expansion elasticity within the 100% range. If the elongation limit of the elastic body sheet is 200% and the elongation limit of the non-woven fabric is 250%, then the elastic complex will have an expansion elasticity of 200%.

Consequently, to obtain sheet elastic complexes which exhibit higher expansion performance, it is important to select the elastic body sheets and sheet backing material with the most appropriate elongatability. The elongatability of most commonly used elastic materials is between 50% and 200% (1.5 to 3 times). Elastic body sheets in this range are appropriate for use in this invention. Elastic bodies with an elongation breaking point of over 500% are also common, but in consideration of the expansion recoverability, a more practical range of extension is 280%, and the range should preferably be kept under.

The elongation limit of the elastic complex is equal to the elongation limit of the non-woven fabric or that of the elastic body, whichever has the lowest numeric value. This is thus the reason for recommending the use of a sheet backing material with a high elongatability in the cross direction, as it is necessary to maximize the performance abilities of the elastic body sheet in order to make the expansion elasticity as great as possible.

FIG. 7 shows the sheet elastic complex of FIGURE 1 in a relaxed state and FIG. 8 shows it in its elongated state. The ratio Q/P of the length Q between the two adjacent bonding sections 3 and 3 of the elastic body sheet 1 when it is in the relaxed [sic] state, to the length P between the same points when the elastic body sheet is in the relaxed state, is the measure of the expandability of the sheet elastic complex. A good Q/P ratio is 1.5 or greater, and an even better ratio is 2.0 to 4.0. If the ratio is less than I.S, the product will lack the appeal of being an elastic body, and if the ratio is greater than 4.0, the product will have little practical value.

In sheet elastic complexes having sheet backings 2 and 2' on both sides, the Q/P ratio can be the same in all of the sections, as shown in (a) of FIG. 9, or it can be different between opposite-facing sections or mutually adjacent sections, as shown in (b) and (c) of FIG. 9. As explained below, this type of structure is beneficial when it is joined to the waist component of a diaper and it is desirable to be able to adjust the state of elongation between the sides and the sections equivalent to the abdomen and back.

Also, as shown in (d) of FIG. 9, the pitch at which the first sheet backing 2 is bonded to elastic body sheet 1 can be different from the pitch at which the second sheet backing 2' is bonded to elastic body sheet I. Or, as shown in (e) of FIG. 9, the positions at which the first sheet backing 2 is bonded to elastic body sheet 1 can be different from the positions at which the second sheet backing 2' is bonded to elastic body sheet 1.

As shown in (f) of FIG. 9, elastic body sheet I, having sheet backing 2, and elastic body sheet I', having sheet backing 2', can be superposed so that the bonding sections are directly opposite one another, or, as shown in (g) of FIG. 9, they can superposed so that the bonding sections are dislocated from each other at a specified pitch.

It is possible to locally control the elongatability, or the maximum extension, of the sheet elastic complex of this invention. The most efficient means of effecting such control over the elongatability is to locally change the gaps between the mutually adjacent bonding sections. For instance, as shown in (a) of FIGURE ID, sheet backings 2 and 2' can be bonded to the two extended elastic body sheets 1 and 1' at the bonding sections 3, which are arranged so that the gaps in the center region are wide and the gaps on the two sides are more narrow. Then, as shown in (b) of FIGURE ID, releasing the tension in the elastic body sheets gives a sheet elastic complex having locally differing bonding section densities. If this product is then stretched apart from the two ends, all of the sections will extend approximately the same amount until the point where the gaps between the bonding sections at the two ends is equal to the length of the sheet backing. At this point, the two ends cease extending, and the extension continues only in the center region.

It is also possible to bond the sheet elastic complex of this invention to other sheet materials, to form an elastic body with a floating structure. In this case, it is possible, as shown in (a) of FIGURE II, to bond the other sheet material M to the top only of sheet backing 2, located on either one of the sides of the sheet elastic complex. This would leave the non-woven fabric of sheet backing 2' exposed on the other side, making possible the use of the soft, bulky feel of the non-woven fabric. It is also possible, as shown in (b) of FIGURE II, to bond other sheet materials M and M' to both sheet backings 2 and 2'.

In the structure shown in (a) and (b) of FIGURE II, the area for bonding sheet backing 2 and/or 2' to the other sheet material(s) M and/or M' can be changed as desired, as shown in FIG. 12, so that the other sheet material M reflects in differing degrees the waveform pattern of sheet elastic complex 5.

The sheet elastic complex of this invention, described above, can offer all the same uses that a normal sheet elastic complex can, and it has the further advantage of being able to be put next to the skin. Thus, it is particularly ideal for use in, for instance, daily necessities such as underwear and socks, in the waist and crotch of disposable diapers, in elastic bandages, and in the sleeve cuffs of surgical gowns.

Many forms of non-woven fabric are suitable sheet backing for the sheet elastic complex when it is used in these capacities. Table 1 gives some examples of suitable non-woven fabrics, and Table 2 lists some good combinations of materials for the elastic body sheet and sheet backing in the sheet elastic complex shown in FIG. 3. However, these are only examples, and this invention is not limited to these specified materials.

TABLE 1

| non-wovens | fibers | web | basis weight | stress (kg/2.5 cm) MD | CD | MC/CD | strain % MD | CD | MD/CD |
|---|---|---|---|---|---|---|---|---|---|
| spunbonded | pp × 2.2 d continuous filaments | random | 30 (g/m²) | 5.3 | 2.2 | 2.4 | 30 | 48 | 1.6 |
| thermally-bonded | PP 2.2 d × 35 m/m | random | 32(–) | 3.9 | 0.6 | 6.5 | 21 | 70 | 3.3 |
| spunlaced | PP 1.5 d × 45 m/m | parallel | 35(–) | 3.7 | 0.8 | 4.6 | 20 | 230 | 11.5 |
| tow | acetate tow | parallel | 40(–) | 5.2 | 0.4 | 13 | 15 | 290 | 19.3 |

TABLE 2

| | Non-woven Fabric | Film | Maximum Stretch-ability | Q/P |
|---|---|---|---|---|
| top | thermally-bonded polypropylene (25 g/m²) | SBES-type polyolefin elastomer single layer (50 mµ) | 260 | 2.4 |
| bottom | thermally-bonded polypropylene (25 g/m²) | | | 2.4 |
| top | thermally-bonded polypropylene (25 g/m²) | SBES-type polyolefin elastomer single layer (50 mµ) | 140 | 2.4 |
| bottom | thermally-bonded polypropylene (25 g/m²) | | | 2.4 |
| top | thermally-bonded polypropylene (25 g/m²) | SBES-type polyolefin elastomer dual layers (50 mµ + 30 mµ) self-adhesion | 300 | 2.8 |
| bottom | thermally-bonded polypropylene (25 g/m²) | | | 2.8 |
| top | thermally-bonded polypropylene (25 g/m²) | SBES-type polyolefin elastomer dual layers (50 mµ + 30 mµ) self adhesion | 280 | 2.8 |
| bottom | thermally-bonded polypropylene (25 g/m²) | | | 2.8 |

FIG. 13 shows a diaper in which the sheet elastic complex of this invention has been applied. It is a normal disposable diaper with an absorptive material set on the inner side of a sheet made from liquid-impermeable material. This means that the invention's sheet elastic complex S is attached to the inner side of thw waist sections W on the front and back of the main diaper body 100 so that sheet backing 2 is exposed on the innser side.

FIG. 14 shows a sheet elastic complex suitable for the waist sections of a diaper. This sheet elastic complex is the same as that shown in FIG. 3, except that sheet backing 2' on one side is shorter than the length of the sheet elastic complex, exposing elastic body sheet 1 on both ends.

FIGS. 15 and 16 show diapers which use the sheet elastic complex shown in FIG. 14. In each of these diagrams, in the waist and abdominal sections of the main diaper body 110, sheet elastic complex S, which is in an elongated state in the cross direction, is affixed at the two ends of elastic body sheet 1 to the sheet of main diaper body 110. This achieves a firm affixation at the two ends C and maintains the original excellent expandability in the center region A.

FIG. 17 shows an underpants-shaped diaper constructed from the sheet elastic complex of this invention, and FIG. 18 shows a cross-section of its waist section. The diaper in these diagrams includes main body 120, formed from liquid-impermeable sheet 121, and forms the shape of underpants so as to suitably cover the waist of the wearer. Belt-shaped member 122, made from a sheet elastic complex, is attached to the waist section of this main body. As shown in FIG. 3, this sheet elastic complex is constructed through the bonding of nonwoven fabrics 2 and 2' to the two sides of elastic body sheet 1. Sheet 121, which forms main body 120, conforms to the waveform of nonwoven fabric 2 located on the outer side. It is therefore possible for the waist of the main diaper body to expand with member 122.

When sanitary product 120, having this construction, is worn, belt-shaped member 122 stays securely on the waist of the wearer because of its excellent expandability, equal to that of a normal rubber belt In addition, nonwoven fabric 2', positioned on the inner side, is what comes in contact with the skin, providing the wearer with a softness and comfort due to the suppleness of the nonwoven fabric itself. Furthermore, as already explained in relation to FIG. 3, multiple, oblong channels 4 form between elastic body sheet 1 and non-woven fabrics 2 and 2', providing a superior comfort due to the breathability and suppleness of channels 4.

Next we will describe the process for manufacturing the sheet elastic complex of the invention.

Basically, the manufacturing process for the sheet elastic complex of the invention includes the following: a process for attaching sheet backing material on at least one side of an elastic body sheet; a process for bonding together the above-mentioned sheet backing material and the above-mentioned elastic body sheet along multiple, oblong, mutually parallel bonding sections; and a process for forming multiple, mutually parallel channels between the above-mentioned sheet backing material and each of the above-mentioned elastic body sheets in the bonded body obtained in the above process, the channels being formed through stretching the above-mentioned sheet backing material past its extension limit in a direction orthogonal to the lengthwise direction of the above-mentioned bonding sections, thus ensuring that the width of the above-mentioned backing material between the mutually adjacent above-mentioned bonding sections is greater than that of the above-mentioned elastic body sheet.

FIG. 19 illustrates one appropriate means of implementing the manufacturing process. Roll pair 131 and 132 act to continuously draw out elastic body sheet I, which has been fed through the rolls. Rolls 133 and 134 act at the same speed to continuously supply the sheet backing material, or non-woven fabrics 2 and 2', along the two sides of the elastic body sheet. Elastic body sheet 1 and non-woven fabrics 2 and 2' then pass between the pair of heated grid rolls, 135 and 136, are chilled between chilling roll pair 137 and 138, and finally pass through guide roll 139 to be wound up by take-up roll 140.

The peripheral speed of chilling rolls 137 and 138 is faster than that of roll pair 131 and 132, and this difference in peripheral speed causes elastic body sheet 1 to stretch.

As shown in detail in FIG. 20, each of the heated grid rolls 135 and 136 have multiple grooves 1371 which extend in the axial direction on the peripheral surface. Cross-sectionally trapezoidal ribs 137-2 form between adjacent grooves. In this example, the groove-to-groove pitch is about 30 mm, the width of the crest of the ribs is about 5 mm, and the height of the ribs is about 3 mm. Both heated rolls 135 and 136 are heated to an appropriate temperature for heat-fusing elastic body sheet 1 and non-woven fabrics 2 and 2' then begin synchronous revolution at a constant velocity so that each rib will continue to meet an opposing rib.

Elastic body sheet 1 and non-woven fabrics 2 and 2' attached to both its sides, elongate through a change from the speed at which only elastic body sheet 1 is stretched. In this elongated state, they pass between heated grid rolls 135 and 136, forming heat-fused bonding sections 3. Thus, the sheet elastic complex is formed.

The added tension is released when the complex emerges between the chilling roll pair 137 and 138, so that elastic body sheet 1 contracts to its original length. At this length only, non-woven fabrics 2 and 2' are slack, and the complex forms the product shown in FIGURE I.

FIG. 21 shows another method of manufacturing the sheet elastic complex shown in FIGURE I. In this example, elastic body sheet 1 and non-woven fabrics 2 and 2' attached to its two sides, pass through heated grid rolls 135 and 136 in an unextended state, bonding together in this step at the bonding sections 3. Next, the complex sheet passes through chilling rolls 137 and 138 to arrive between the draw roll pair 141 and 142. The peripheral speed of the draw roll pair 141 and 142 is faster than that of the chilling roll pair 137 and 138, causing a drawing out of the complex sheet during this interval. Then the tension is released, and take-up roll 140 winds the complex sheet. In this drawing-out process, the non-woven fabric is stretched past its extension limit, so that it will not return to its original length when the tension is released, thus forming a sheet elastic complex with the structure shown in FIGURE I.

In these examples, heated grid rolls 135 and 136 are used as the means of bonding elastic body sheet 1 and non-woven fabrics 2 and 2' but it is also possible to use ultrasonic fusion or to cement the members with an adhesive.

It is also possible to make an elastic complex which is pleated on both sides by first making elastic complexes composed of an elastic body sheet with non-woven fabric bonded to it in a waveform on only one side, then bonding two such sheets together.

Or, the desired sheet elastic complex can be easily constructed by taking two bonded bodies consisting of one sheet of non-woven fabric and an elastic body sheet, bonding the two bonded bodies together on the elastic body sheet surfaces, elongating the complex, and then releasing the tension.

FIG. 22 illustrates yet another method of manufacturing the sheet elastic complex. This process is made up of the following processes: process 51 for forming the sheet through molten extrusion of raw elastomer resin; process 52 for chilling the sheet thus formed; process 53 for joining the sheet with non-woven fabric by pressing them together; process S4 for provisionally securing the two parts together through the use of a press; process S5 for completing the bonding of this provisionally secured sheet through partial heating and pressure bonding between the heated grid rolls; and finally, process 56 for winding the product.

FIG. 23 is a schematic drawing of a device for implementing the method shown in FIG. 22. In FIG. 23, symbol 150 is the molten extruder composed of hopper 151, which accepts the raw elastomer resin, extruder 152, and die 153; 154 is the chilling roll which accepts the extruded material; 155 is the non-woven fabric supply roll; 156 and 157 are the press rolls for provisional securement; 158 is a heated grid roll; and 159 is the product take-up roll.

As shown in FIG. 24, heated grid roll 158 has multiple ribs which form rings perpendicular to the shaft center. Thus, unlike in the previously discussed processes, the elastic body sheet and the non-woven fabric are bonded along multiple, mutually parallel bonding sections which extend in the machine direction. The desired sheet elastic complex is obtained by extending this bonded body in the cross direction past the reversion limit of the non-woven fabric, then releasing the tension.

FIG. 25 shows one example of a process for applying an elastic complex of this invention during the formation of crotch gathers in the production of disposable diapers, the elastic complex being expandable in the machine direction. In the FIGURE, sheet elastic complex 160, cut into tape of the desired width, is continuously drawn out from roll 161, cutter 162 cuts the tape into appropriate lengths, moving drum 163 acts to supply it to the top of non-woven fabric 164. Then the public domain method of hot melting, not shown in the FIGURE, is applied at the positions of contact between the tape and the non-woven fabric.

Non-woven fabric 164 is continuously drawn out from roll 165 at a constant speed, its travel speed being set to a value slightly higher than the peripheral speed of moving drum 163. Thus when the sheet elastic complex tape feeding onto non-woven fabric 164 from moving drum 163 is secured at one end to non-woven fabric 164, the remaining portion of the tape is stretched out. The stretched tape is then secured to filament 164. As a result, when sheet elastic complex tape 160' separates from moving drum 163, it contracts along with the non-woven fabric, due to its own reversibility. This forms floating crotch gathers with exceptionally good expandability.

FIG. 26 shows a sample of an application for a sheet elastic complex 5 of this invention during the formation of waist gathers in the production of disposable diapers, the elastic complex having bonding sections extending in the machine direction-in other words, having expandability in the cross direction.

Sheet elastic complex 5 is cut in the cross direction into specified lengths by cutter 170, and sheet elastic complex tape 171 is stretched in the cross direction as the progressively separating pair of belts 172 and 173 grip them at both ends. Then, using the hot melt method, sheet elastic complex tape 171, still in this gripped state, is secured to the positions on the main diaper body (not illustrated) that are comparable to the waist. Then the comparable waist sections are cut apart and the tension released, forming floating waist gathers with exceptionally good expandability.

To increase the efficiency of industrial handling it will be beneficial to incorporate the manufacturing process for the elastic complex and the process for bonding the elastic process to products, a series of processes, into the manufacturing process for a diaper.

Next we will discuss specific examples of manufacturing processes for the sheet elastic complex of this invention and processes which incorporate the complexes into sanitary products.

EXAMPLE 1

The Elastic Complex

For the base elastic material, we prepared a 14 roll of three-layer extruded film having a width of an approximately 50, with approximately 15 of SEBS resin (Mitsubishi petrochemical-made Rabaron) on both sides of a core of 20 m of polyether polyurethane resin film. The elongation breaking point of this film was 420% in the machine direction. The film also had strong ultrasonic sealing properties. For the non-woven fabric, we prepared two rolls of 20 R/m$^2$ dry spot bond P, P non-woven fabric (made by U.S. Beldex [phonetic rendering]). The elongation breaking point of this non-woven fabric in the machine direction was 38%. In a process like that of FIG. 19, we elongated the above-mentioned elastic material by approximately a factor of 3 between roll 14 (at about 20 m/min) and roll 15 (at about 60 m/min). Then, at the position of rolls 16 and 17, we supplied two layers of non-woven fabric above and below, so as to sandwich the elastic material in between.

We prepared a roll having grids in the anvil at 25 m/m intervals and equipped with a rotary ultrasonic fusion device (Brunson-made), passed the three-layer sheet through it at a rate of 62 m/min, then wound the sheet up in its elongated state. When some of this three-layer, partially bonded sheet was cut off, it relaxed to a tension-free state to form an elastic complex which was pleated on both sides and had a limit elongation rate in the machine direction of 185%. The surface ratio of the bonded sections ((A+B)/A)×100% was approximately 20%, and Q/P was an increase by approximately a factor of 2.7.

Bonding the Elastic Complex to the Main Product Body

For the product, we removed the linear gathers from the outer side of a commercial disposable diaper (Proctor & Gamble-made Pampers, size M). We elongated the top sheet at the sideclap position where the gathers were to be formed and the pleated portion of the non-woven fabric in the above-mentioned elastic complex. Keeping these two parts elongated, we bonded them together with a permanent hot-melt adhesive. Gathers in the crotch of this diaper had an elongation rate of about 180%, so that almost none of the elastic performance of the complex was lost. In a test of approximately 30 such pieces on five babies, mothers interviewed attested that there was very little leakage and that the surface was extremely soft.

EXAMPLE 2

The Elastic Complex

For the elastic member, we used the inflation method to form a cylindrical film with a width of 30, using a polyolefine elastomer (Tonen Chemical-made Raprez), of which the main components were E.U.A. and butadiene. This elastic member had an elongation breaking point of 520% and had properties which made it lend itself to self-adhesion when film was superposed on it and pressed. We stored this inflation-formed cylindrical film as it was in the form of a take-up roll.

We manufactured the elongatable non-woven fabric in the following manner. We produced a non-woven fabric with mutually confounded fibers by treating a random fiber weave (Helges [phonetic rendering]-made Random Card), made from 2 d×51 m/m p, P (polypropylene) Side-by-Side Coniugate fiber (ES complex fiber made by Chisso), with a high-pressure jet in a porous belt. We obtained a non-woven fabric with an extremely high level of elongatability by subjecting the above fabric to pressure dehydration, then causing drying shrinkage in it by sending it through a 130° C. hot-air drier in the auto feed state by a factor of 1.6. The elongation breaking point of the resulting non-woven fabric was 190%. We prepared two rolls of this nonwoven fabric.

Using the device shown in FIG. 21, we sandwiched a core of the above-mentioned elastic member between two layers, upper and lower, of the elongatable non-woven fabric, and passed this complex through rolls heated to 100° C. at a speed of 30 m/min, making a three-layer complex sheet with a lateral stripe thermal bonding pattern. The thermally bonded section (A) was 3 m/m, and the unbonded section (B) was 8 m/m.

We elongated this complex sheet by approximately a factor of 2.5, so that the unbonded sections of both the non-woven fabric and the elastic member were elongated. We then released the tension in the complex sheet, thus obtaining an elastic complex with an elongatability of about 150%. Q/P for this complex was an increase by approximately a factor of 2.5. This elastic complex had a structure consisting of a two-layer elastic member, the layers bonded together through self-adhesion, with pleats formed in the non-woven fabric on both sides.

Bonding the Elastic Complex to a Region of the Product

We obtained the elastic complex through the above process. We cut into strips the complex sheet consisting of the elastic member and the non-woven fabric prior to elongation, then wound these sheets into 10 rolls processed into the form of tape. (Winding the tape after elongation will result in a loss of machine direction expandability, as the elongation tension will bring about a stress relaxation in the elastic member. And winding the complex elastic body in a tension-free state, after it has been elongated, then relaxed, will make the rolls overly bulky, unsuitable for a raw material.)

In a process like that shown in FIG. 26, we cut the 15 m/m tape sheets described above into specified lengths, simultaneously elongating them by a factor of 2.4, then we secured the complex sheet to the part of the diaper comparable to the crotch gathers by hot melting the non-woven fabric surface to the diaper's surface material. In a tension-free state, the elastic body thus obtained had an exceptionally good expandability, with an elongatability of 140%.

EXAMPLE 3

The Elastic Body

For the elastic member, we formed a 30 m film by extruding a polyolefine elastomer elastic sheet with V.L.L.D.P.E. as its main component (made by Mitsui Toatsu Chemicals) from molten dies. We then stretched this film in the machine direction so that it had a structure that was easily expandable in the cross machine direction. It had an elongation breaking point at about 180% in the machine direction and at about 420% in the cross direction.

For the non-woven fabric, we made an approximately 35 g/m$^2$ parallel weave (using Holingsworth-made Tandem Master Card) from 2.2 d×45 m/m of polypropylene fibers (made by Daiwabo), then mutually confounded the fibers with a high-pressure water jet (50 to 60 kg/cm) on a cylinder equipped with multiple latticed holes and a dehydration zone. We then dried the weave to obtain a non-woven fabric with a 25 g/m$^2$ soft feel. The structure of this non-woven fabric made it easily elongatable in the cross direction, the elongation breaking point in the cross direction being at 220%, while that in the machine direction was at approximately 58%. Using a process like that shown in FIG. 23, we chilled at approximately 50 m/min the film obtained by molten extrusion of the above-mentioned elastic member, guided the above-mentioned non-woven fabric onto a roll, and pressed the non-woven fabric and the film together so that the film and the non-woven fabric were in a provisionally secured state. We then fed one side of this complex sheet through a heated grid roll like that shown in FIG. 24. The grid roll, whose surface was heated to approximately 110° C., contacted the complex from the non-woven fabric side. Bonding sections (A) were approximately 2 m/m and the width of the non-bonding sections (B) was approximately 6 m/m. In this manner we obtained a complex sheet with the nonwoven fabric film thermally bonded in a partially linear pattern. By elongating this sheet in the cross direction by approximately a factor of 2.8 (180%), then relaxing it into a tension-free state, we obtained an exceptionally expandable elastic complex with pleated non-woven fabric on one side. Q/P for this complex was an increase by approximately a factor of 2.8.

We produced a 500 m roll of the above continuously obtained complex sheet, winding the sheet up without having elongated it. It was possible to securely wind it out again from the roll, as the layer of non-woven fabric prevented self-adhesion. Then we cut off strips of this sheet, superposed two strips on the exposed elastic member surfaces, and joined the superposed strips by cold-pressing them, which caused self-adhesion in the like films. We elongated the complex in this superposed state in the cross direction by about a factor of 2.7 (170%). When we relaxed it to a tension-free state, we had obtained an exceptionally expandable elastic complex with non-woven fabric pleats on both sides.

Bonding the Elastic Complex to a Region of the Product

We cut the above complex sheets into strips and prepared two sheet rolls with a width of approximately 180 m/m. We superposed two 180 m/m sheets so that the elastic members were adjoined, then exerted pressure so that the two sheets exhibited self-adhesion and reached a provisionally secured state.

Next, we used a 120° C. smooth surface roll to heat and press both sides of the 30 m/m sections extending in from the two ends. Then, using a process like that of FIG. 26, we cut this complex sheet, which was completely thermocompressed on both sides of the 30 m/m sections and provisionally secured in the central 120 m/m section, into 50 m/m wide strips. As we cut, we expanded and elongated the strips in the cross direction so that the pressed sections on both ends could be inserted into the belts and so that the whole complex would increase by approximately a factor of 2.

In the elongation, we elongated the central 120 m/m section to approximately 300 m/m, or by a factor 2.5, without elongating the two 30 m/m sections on the ends (a total of 60 m/m). Keeping the strips elongated, we bonded the non-woven fabric part of the elastic complex to the surface material of the part of the disposable diaper comparable to the waist. Then we attached adhesive tape, the binding means, to the two completely secured 30 m/m ends, cut the complex off onto a single diaper, and released the tension. Thus we produced a baby diaper with a waist structure equipped with a tape and an exceptionally expandable elastic body.

What is claimed is:

1. A sheet elastic complex
comprising a non-elastic backing sheet which has been bonded along multiple, oblong, mutually parallel bonding sections to at least one major surface of a planar elastic sheet under heating conditions, the width of the backing sheet between adjacent ones of said bonding sections being greater than that of said elastic sheet to form channels in combination with the planar elastic sheet, wherein said bonding sections have a width X, and non-bonding sections between said bonding sections have a width Y, with the ratio $$\frac{x}{(x+y)} \times 100\%$$

being less than 50%, and wherein Q is the length between said bonding sections in a stretched state of said sheet elastic complex, and P is the length between said bonding sections in a relaxed state of said sheet elastic complex, and a ratio of Q/P is equal to or greater than 1.5.

2. A sheet elastic complex as stated in claim 1 in which the width of the above-mentioned bonding sections is less than 50% of the roll sum of the width of these bonding sections and the intervals between each two adjacent bonding sections.

3. A sheet elastic complex as stated in claim 1 in which the height of the above-mentioned channels in the widthwise direction is greatest in the center region and decreases progressively towards the two ends.

4. A sheet elastic complex as stated in claim 1 in which the above-mentioned backing sheet is made of non-woven fabric.

5. A sheet elastic complex as stated in claim 1 in which the above-mentioned backing sheet is a liquid-impermeable sheet.

6. A sheet elastic complex as stated in claim 5 in which the material for the above-mentioned liquid-impermeable sheet is selected from the group comprised of polyethylene, polypropylene, nylon, and polyester.

7. A sheet elastic complex as stated in claim 1 in which the above-mentioned elastic body sheet is a sheet made from a material chosen from the group comprised of natural rubber, synthetic rubber, polyurethane, polyurethane mellitic-blown non-woven fabric, styrene-butadiene block copolymer, and polyolefine.

8. A diaper to which a sheet elastic complex as stated in claim 1 is affixed in the waist section.

9. An underpants-shaped sanitary product constructed from a sheet elastic complex as stated in claim 1.

10. A sheet elastic complex
comprising first and second non-elastic backing sheets which have been bonded along multiple, oblong, mutually parallel bonding sections to opposing surfaces of a planar elastic sheet under heating conditions, the width of each of the backing sheets between adjacent ones of said bonding sections being greater than that of said elastic sheet to form channels in combination with the planar elastic sheet, wherein said bonding sections have a width X, and non-bonding sections between said bonding sections have a width Y, with the ratio $$\frac{x}{(x+y)} \times 100\%$$

being less than 50%, and wherein Q is the length between said bonding sections in a stretched state of said sheet elastic complex, and P is the length between said bonding sections in a relaxed state of said sheet elastic complex, and a ratio of Q/P is equal to or greater than 1.5.

11. A sheet elastic complex as stated in claim 10 in which the height of the above-mentioned channels in the widthwise direction is greatest in the center region and decreases progressively towards the two ends.

12. A sheet elastic complex as stated in claim 10 in which the bonding sections of the above-mentioned elastic body sheet and the above-mentioned first backing sheet and the bonding sections of the above-mentioned elastic body sheet and the above-mentioned second backing sheet are located in the same positions.

13. A sheet elastic complex as stated in claim 12 in which the maximum height of each channel formed between the above-mentioned elastic body sheets and the above-mentioned first and second backing sheet is greater than the maximum height of its adjoining channel.

14. A sheet elastic complex as stated in claim 12 in which the interval between the above-mentioned bonding sections is wide in the center region of the above-mentioned sheet elastic complex and narrower in the other regions.

15. A sheet elastic complex as stated in claim 11 in which the size of the above-mentioned first backing sheet is large enough to cover almost the entire above-mentioned elastic body sheet, and in which the size of the above-mentioned second backing sheet is only large enough to cover the central region of the above-mentioned elastic body sheet.

16. A diaper to which a sheet elastic complex as stated in claim 15 is affixed in the waist section.

17. A sheet elastic complex as stated in claim 10 in which one bonding section between the above-mentioned elastic body sheet and the above-mentioned second backing sheet is located on every other bonding section between the above-mentioned elastic body sheet and the above-mentioned first backing sheet.

18. A sheet elastic complex as stated in claim 10 in which each bonding section between the above-mentioned elastic body sheet and the above-mentioned first non-elastic backing sheet is located between adjacent bonding sections between the above-mentioned elastic body sheet and the above-mentioned second non-elastic backing sheet.

19. A sheet material in which one of the first and second backing sheets of the sheet elastic complex as stated in claim 10 is bonded to another sheet material to form a floating structure.

20. A sheet elastic complex comprising:
at least one non-elastic backing sheet; and
a planar elastic sheet;
wherein the at least one backing sheet has been bonded to the elastic sheet in a relaxed state, along multiple, mutually parallel bonding sections, and the at least one backing sheet has been stretched past its extension limit in a direction orthogonal to the lengthwise direction of parallel bonding sections to form channels in the backing sheet in combination with the planar elastic sheet, wherein said bonding sections have a width X, and non-bonding sections between said bonding sections have a width Y, with the ratio $$\frac{x}{(x+y)} \times 100\%$$

being less than 50%, and wherein Q is the length between said bonding sections in a stretched state of said sheet elastic complex, and P is the length between said bonding sections in a relaxed state of said sheet elastic complex, and a ratio of Q/P is equal to or greater than 1.5.

21. The sheet elastic complex of claim 20 in which at least one of the backing sheets is a non-woven fabric.

22. A sheet elastic complex comprising:

a planar elastic sheet; and
a pair of non-elastic backing sheets respectively superposed on each side of said elastic sheet;
wherein each said non-elastic backing sheet is bonded to the elastic sheet in a relaxed state, along multiple, mutually parallel bonding sections, and each of the non-elastic backing sheets is stretched past its extension limit in a direction orthogonal to each lengthwise direction of parallel bonding sections to form channels in the backing sheet in combination with the planar elastic sheet, wherein said bonding sections have a width X, and non-bonding sections between said bonding sections have a width Y, with the ratio $$\frac{x}{(x+y)} \times 100\%$$

being less than 50%, and wherein Q is the length between said bonding sections in a stretched state of said sheet elastic complex, and P is the length between said bonding sections in a relaxed state of said sheet elastic complex, and a ratio of Q/P is equal to or greater than 1.5.

23. A stretchable sheet composite comprising:
a non-elastic sheet having an expansive surface formed by stretching the sheet past its extension limits in a direction orthogonal to the lengthwise direction of parallel bonding regions between the non-elastic sheet and an elastic sheet; and
said elastic sheet being essentially uniaxially stretchable, said elastic sheet having been heat-bonded in a relaxed state to said surface of the non-elastic sheet resulting in the formation of a number of substantially parallel, elongated bonding regions extending transverse to said axial direction of stretch to define bond-free regions between adjacent parallel bonding regions in said stretchable sheet composite, wherein said bonding regions have a width X, and said bond-free regions have a width Y, with the ratio $$\frac{x}{(x+y)} \times 100\%$$

being less than 50%, and wherein Q is the length between said bonding regions in a stretched state of said sheet composite, and P is the length between said bonding regions in a relaxed state of said sheet composite and a ratio of Q/P is equal to or greater than 1.5.

24. The stretchable sheet composite of claim 23, wherein said elastic sheet is more elongatable in said one direction than transverse to said one direction.

25. The stretchable sheet composite of claim 23, wherein said elastic sheet comprises polyolefin elastomers.

26. The stretchable sheet composite of claim 23, further comprising a second non-elastic sheet intermittently bonded to said elastic sheet so that first and second non-elastic sheets flank said elastic sheet.

27. The stretchable sheet composite of claim 23, wherein said non-elastic sheet comprises a non-woven material.

28. The stretchable sheet composite of claim 23, wherein said bonding regions have a width greater than 0.5 mm.

29. The stretchable sheet composite of claim 28, wherein said width is between 1 mm and 10 mm.

30. The stretchable sheet composite of claim 23, wherein a ratio of a width dimension between two adjacent bonding regions when the elastic sheet is in an elongated state, to the width dimension when the elastic sheet is in a relaxed state, is at least 1.5.

31. The stretchable sheet composite of claim 30, wherein the ratio is from 2.0 to 4.0.

32. The stretchable sheet composite of claim 30, wherein the ratio is different between two adjacent non-bonding regions.

33. A stretchable sheet composite comprising:

an elastic sheet having been heat-bonded to a non-elastic, non-woven fabric by a number of substantially parallel, elongated bonding regions extending in one direction to define bond-free, stretchable regions between adjacent parallel bonding regions in said stretchable sheet composite, such stretchable sheet composite being more stretchable transverse to said bonding regions than along said bonding regions, said non-elastic, non-woven fabric sheet having been stretched beyond its extension limit in a direction orthogonal to the lengthwise direction of said parallel bonding regions, wherein said bonding regions have a width X, and said bond-free regions have a width Y, with the ratio $$\frac{x}{(x+y)} \times 100\%$$

being less than 50%, and wherein Q is the length between said bonding regions in a stretched state of said sheet composite, and P is the length between said bonding regions in a relaxed state of said sheet composite and a ratio of Q/P is equal to or greater than 1.5.

34. The elastic composite sheet of claim 33, wherein said elastic sheet is uni-axially stretchable transverse to said bonding regions.

35. The elastic composite sheet of claim 33, wherein said non-woven fabric sheet is a spunlace non-woven fabric obtained through a water-jet process.

36. The elastic composite sheet of claim 33, wherein said non-woven fabric sheet comprises hydrophobic fibers.

37. The elastic composite sheet of claim 36, wherein said hydrophobic fibers include synthetic staple fibers having a denier within the range of 1.5–3.

38. The elastic composite sheet of claim 33, wherein said non-woven fabric has a basis weight of $25-35 g/m^2$.

39. A stretchable compositive material comprising:

a pair of stretchable sheet composites, each of said sheet comprising a non-elastic sheet, and an elastic sheet intermittently bonded to said non-elastic sheet at a number of parallel securement portions to define non-secured, stretchable portions of each said sheet composites, said pair of stretchable sheet composites being superposed to each other by joining said elastic sheets pair of composites to each other so as to flank said elastic sheets between said non-elastic sheets, each of said non-elastic sheets having been stretched beyond its extension limit in a direction orthogonal to the lengthwise direction of said parallel securement portions, wherein said securement portions have a width X, and said non-secured portion have a width Y, with the ratio $$\frac{x}{(x+y)} \times 100\%$$

being less than 50%, and wherein Q is the length between said securement portions in a stretched state of each said sheet composite, and P is the length between said securement portions in a relaxed state of said sheet composite and a ratio of Q/P is equal to or greater than 1.5.

40. The stretchable composite material of claim 39, wherein said securement portions of respective stretchable sheet composites coincide with each other.

41. The stretchable composite material of claim 39, wherein said securement portions in each of said stretchable sheet composites comprise a number of parallel, elongated bonding portions to define non-bonding, stretchable portions therebetween.

42. The stretchable composite material of claim 41, wherein said elongated bonding portions of respective stretchable sheet composites coincide with each other.

43. The stretchable composite material of claim 41, wherein said elongated bonding portions of respective stretchable sheet composites are staggered from each other.

44. A disposable absorbent article having a waist section comprising:

a main body including a liquid impermeable sheet, and an absorbent material placed on the liquid permeable sheet; and an elastic composite disposed along said waist section for forming a waist gather, said elastic composite comprising outer and inner non-elastic sheets each of which has been stretched beyond its extension limit in a direction orthogonal to the lengthwise direction of parallel heat-bonding between each of said non-elastic sheets and an elastic sheet flanked thereby, each of said outer and inner non-elastic sheets being gathered into a number of pleats and being bonded to said elastic sheet substantially along nadirs of said pleats so as to define spaced bonding regions, providing said bonding areas, substantially parallel to one another, said inner non-elastic sheet being bonded to said main body substantially along apices of said pleats so as to form said waist gather, wherein said bonding regions have a width X, and non-bonding regions between said bonding regions have a width Y, with the ratio $$\frac{x}{(x+y)} \times 100\%$$

being less than 50%, and wherein Q is the length between said bonding regions in a stretched state of said elastic composite, and P is the length between said bonding regions in a relaxed state of said elastic composite, and a ratio of Q/P is equal to or greater than 1.5.

45. A process for manufacturing a sheet elastic complex which includes a non-elastic backing sheet material on at least one side of an elastic body sheet, comprising the steps of:

bonding the backing sheet material and elastic body sheet at multiple, oblong, and mutually parallel bonding sections under heating conditions;

and forming multiple, mutually parallel channels between the backing sheet material and the elastic body sheet, the channels being formed through stretching the backing sheet material past its extension limit in a direction orthogonal to the lengthwise direction of the bonding sections, thus ensuring that the width of the backing sheet material between the mutually adjacent bonding sections is greater than that of the elastic body sheet, wherein said bonding sections have a width X, and non-bonding sections between said bonding sections have a width Y, with the ratio $$\frac{x}{(x+y)} \times 100\%$$

being less than 50%, and wherein Q is the length between said bonding sections in a stretched state of said sheet elastic complex, and P is the length between said bonding sections in a relaxed state of said sheet elastic complex, and a ratio of Q/P is equal to or greater than 1.5.

46. A process as stated in claim 45 in which the backing sheet material is a non-woven fabric.

47. A process for manufacturing a sheet elastic complex which includes drawing an elastic body sheet from a roll;

bonding each non-elastic backing sheet material to the elastic body sheet at multiple, oblong, and mutually parallel bonding sections by bonding the three-ply complex from both sides using a heated grid roll having protrusions which extend in the axial direction;

and forming multiple, mutually parallel channels between the non-elastic backing sheet material and the elastic body sheet, the channels being formed through stretching the non-elastic backing sheet material past its extension limit in a direction orthogonal to the lengthwise direction of the bonding sections, thus ensuring that the width of the backing sheet material between the mutually adjacent bonding sections is greater than that of the elastic body sheet, wherein said bonding sections have a width X, and non-bonding sections between said bonding sections have a width Y, with the ratio $$\frac{x}{(x+y)} \times 100\%$$

being less than 50%, and wherein Q is the length Y, with the bonding sections in a stretched state of said sheet elastic complex, and P is the length between said bonding sections in a relaxed state of said sheet elastic complex, and a ratio of Q/P is equal to or greater than 1.5.

48. A method of manufacturing a uniaxially stretchable, sheet composite comprising the steps of:

feeding a continuous, uniaxially stretchable elastic sheet in the direction transverse to said uniaxial direction so that said elastic sheet is introduced in a substantially relaxed state;

introducing a continuous, non-elastic sheet in the direction transverse to said uniaxial direction in juxtaposition with said stretchable elastic sheet;

heat-bonding said elastic sheet in the relaxed state to said non-elastic sheet to form a number of intermittent parallel heat-bonding regions and stretching the non-elastic sheet of the bonded composite beyond its extension limit in a direction orthogonal to the longitudinal direction of the parallel bonding regions, wherein said heat-bonding regions have a width X, and said bond-free regions have a width Y, with the ratio $$\frac{x}{(x+y)} \times 100\%$$

being less than 50%, and wherein Q is the length between said heat-bonding regions in a stretched state of each said stretchable sheet composite, and P is the length between said heat-bonding regions in a relaxed state of said stretchable sheet composite and a ratio of Q/P is equal to or greater than 1.5.

49. The method of claim 48 wherein said continuous, non-elastic sheet is more elongatable in a width direction than in a longitudinal direction, and in said introducing step, the longitudinal direction of the non-elastic sheet is directed toward said one direction.

50. The method of claim 48, wherein after said bonding step, the resultant composite is stretched transverse to said one direction so that the non-elastic sheet is a non-bonding regions permanently elongated, said non-bonding regions of the non-elastic sheet being gathered by said elastic sheet when the stretched composite elastically contracts.

51. The method of claim 48, wherein in said bonding step, the elastic and non-elastic sheets are intermittently bonded by a number of parallel, elongated bonding regions extending in said one direction.

52. The method of claim 48, wherein said feeding step is performed by extruding molten elastomer resin onto said non-elastic sheet.

\* \* \* \* \*

UNITED STATES PATENT AND TRADEMARK OFFICE
CERTIFICATE OF CORRECTION

PATENT NO. : 5,576,090
DATED : November 19, 1996
INVENTOR(S) : Migaku Suzuki

It is certified that error appears in the above-indentified patent and that said Letters Patent is hereby corrected as shown below:

In column 3, line 2, "figure one" should be --Fig. 1--.

In column 5, line 38, "or" should be --of--;
        line 47, after "can" insert --be--.

In column 8, line 1, "I" should be --1--;
        line 6, "I" should be --1--;
        line 7, "I" should be --1--;
        line 17, "ID" should be --1D--;
        line 21, "ID" should be --1D--;
        line 33, "II" should be --2--;
        line 39, "II" should be --2--;
        line 41, "II" should be --2--.

In column 9, line 54, "thw" should be --the--;
        line 56, "innser" should be --inner--.

UNITED STATES PATENT AND TRADEMARK OFFICE
CERTIFICATE OF CORRECTION

PATENT NO. : 5,576,090
DATED : November 19, 1996
INVENTOR(S) : Migaku Suzuki

It is certified that error appears in the above-indentified patent and that said Letters Patent is hereby corrected as shown below:

In column 10, line 64, "I" should be --1--.

In column 11, line 10, "1371" should be --137-1--;
              line 30, "I" should be --1--;
              line 32, "I" should be --1--;
              line 46, "I" should be --1--.

In column 12, line 1, "S4" should be --54--;
              line 2, "S5" should be --55--.

In column 13, line 66, "Coniugate" should be --Conjugate--.

In column 14, line 29, after "into", delete --10--.

UNITED STATES PATENT AND TRADEMARK OFFICE
CERTIFICATE OF CORRECTION

PATENT NO. : 5,576,090
DATED : November 19, 1996
INVENTOR(S) : Migaku Suzuki

It is certified that error appears in the above-indentified patent and that said Letters Patent is hereby corrected as shown below:

In column 19, line 54, after "sheets", insert --of said--.

In column 21, line 42-43, delete "Y, with the" and insert --between said--.

Signed and Sealed this

Twenty-ninth Day of April, 1997

Attest:

BRUCE LEHMAN

Attesting Officer

Commissioner of Patents and Trademarks